United States Patent
Fu et al.

(10) Patent No.: US 8,519,168 B2
(45) Date of Patent: Aug. 27, 2013

(54) PROCESS AND INTERMEDIATES FOR THE SYNTHESIS OF 1,2-SUBSTITUTED 3,4-DIOXO-1-CYCLOBUTENE COMPOUNDS

(75) Inventors: Xiaoyong Fu, Edison, NJ (US); Frank Bruno Guenter, Ruswil (CH); Agnes S. Kim-Meade, Fanwood, NJ (US); Kenneth Stanley Matthews, Stockton, CA (US); Mathew Thomas Maust, Westfield, NJ (US); Timothy L. McAllister, Westfield, NJ (US); David J. Moloznik, legal representative, Philadelphia, PA (US); Gerald Werne, Ketsch (DE); Jason L. Winters, East Windsor, NJ (US); Jianguo Yin, Plainsboro, NJ (US); Shuyi Zhang, Parsippany, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 221 days.

(21) Appl. No.: 12/665,913

(22) PCT Filed: Jul. 1, 2008

(86) PCT No.: PCT/US2008/008187
§ 371 (c)(1),
(2), (4) Date: Feb. 25, 2011

(87) PCT Pub. No.: WO2009/005801
PCT Pub. Date: Jan. 8, 2009

(65) Prior Publication Data
US 2011/0160469 A1   Jun. 30, 2011

Related U.S. Application Data

(60) Provisional application No. 60/958,317, filed on Jul. 3, 2007, provisional application No. 60/958,313, filed on Jul. 3, 2007, provisional application No. 60/958,311, filed on Jul. 3, 2007.

(51) Int. Cl.
*C07D 307/40* (2006.01)
(52) U.S. Cl.
USPC .......................................................... 549/494
(58) Field of Classification Search
USPC .......................................................... 549/494
See application file for complete search history.

(56) References Cited

U.S. PATENT DOCUMENTS

| | | | |
|---|---|---|---|
| 7,071,342 B2 | 7/2006 | Yin et al. | |
| 7,132,445 B2 | 11/2006 | Taveras et al. | |
| 7,462,740 B2 | 12/2008 | Yin et al. | |
| 7,910,775 B2 | 3/2011 | Yin et al. | |
| 7,947,720 B2 | 5/2011 | Taveras et al. | |
| 7,964,646 B2 | 6/2011 | Taveras et al. | |
| 8,207,221 B2 | 6/2012 | Hu et al. | |
| 2004/0209946 A1* | 10/2004 | Yin et al. | 514/471 |
| 2005/0192345 A1 | 9/2005 | Hu et al. | |
| 2008/0045489 A1 | 2/2008 | Chao et al. | |

FOREIGN PATENT DOCUMENTS

| | | |
|---|---|---|
| JP | 3-95144 | 4/1991 |
| WO | 2004/094398 | * 11/2004 |
| WO | 2005/068460 | * 7/2005 |
| WO | 2008/005570 A1 | 1/2008 |

OTHER PUBLICATIONS

Rampino, L.D., et al. "Applicability of Palladium Synthetic High Polymer Catalysts", Journal of American Chemistry Society, 1941, vol. 63, p. 3268.
International Preliminary Report on Patentability in connection with PCT/US2008/008187, issued Jan. 5, 2010.

* cited by examiner

*Primary Examiner* — Taofiq A Solola
(74) *Attorney, Agent, or Firm* — Eric A. Meade; Valerie J. Camara

(57) ABSTRACT

This application discloses a novel process for the preparation of 1,2-substituted 3,4-dioxo-1-cyclobutene compounds, which have utility, for example, in the treatment of CXC chemokine-mediated diseases, and intermediates useful in the synthesis thereof.

24 Claims, No Drawings

PROCESS AND INTERMEDIATES FOR THE SYNTHESIS OF 1,2-SUBSTITUTED 3,4-DIOXO-1-CYCLOBUTENE COMPOUNDS

CROSS REFERENCE TO RELATED APPLICATIONS

This application is commencing national stage examination pursuant to 35 U.S.C. §371 from International patent application No. PCT/US2008/008187 filed in the U.S. PCT receiving office on Jul. 1, 2008, which international application is based on and claims the priority of U.S. Provisional Patent Application Ser. Nos. 60/958,317 filed Jul. 3, 2007, 60/958,313, filed Jul. 3, 2007, and 60/958,311, filed Jul. 3, 2007. Each of the aforementioned PCT and Provisional applications is incorporated in its entirety by reference as if fully set forth herein.

FIELD OF THE INVENTION

This application discloses a novel process for the preparation of 1,2-substituted 3,4-dioxo-1-cyclobutene compounds, which have utility, for example, in the treatment of CXC chemokine-mediated diseases, and intermediates useful in the synthesis thereof.

BACKGROUND OF THE INVENTION

Identification of any publication, patent, or patent application in this section or any section of this application is not an admission that such publication is prior art to the present invention.

The preparation of 1,2-substituted 3,4-dioxo-1-cyclobutene compounds, for example, 2-Hydroxy-N,N-dimethyl-3-[[2-[[1(R)-(5-methyl-2-furanyl)propyl]amino]-3,4-dioxo-1-cyclobuten-1-yl]amino]benzamide (compound of formula I):

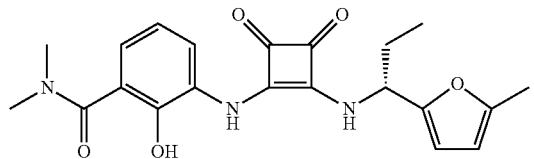

Formula I has been described in U.S. Pat. Nos. 7,123,445 (the '445 patent), issued Nov. 7, 2006, and 7,071,342 (the '342 patent), issued Jul. 4, 2006, the disclosure of each of which is incorporated herein in its entirety by reference. For examples of the preparation of the compound of Formula I, see the '455 patent at cols. 491 to 492, cols. 196 to 197, and cols. 251 to 256, and see the '342 patent, for example, at cols. 22 through 24.

Another example of the preparation of a 1,2-substituted 3,4-dioxo-1-cyclobutene compound, the preparation the 2-hydroxy-N,N-dimethyl-3-[[2-[[1(R)-[5-methyl-4-(1-methylethyl)-2-furanyl]propyl]amino)-3,4-dioxo-1-cyclobuten-1-yl]amino]-benzamide (the compound of Formula II),

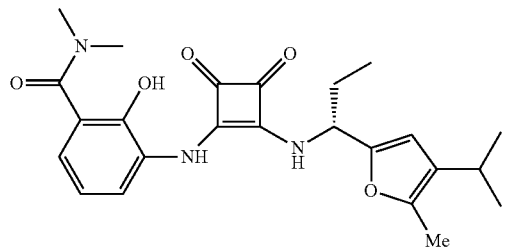

Formula II is described in U.S. provisional patent application 60/819,541 (the '541 application) filed Jul. 7, 2006, the disclosure of which is incorporated by reference in its entirety. An example of the preparation of the compound of Formula II can be found in Example 2 of the '541 application. The aforementioned preparation schemes for the compounds of Formulae I and II are incorporated herein by reference in their entirety.

The synthesis method for preparing 1,2-substituted 3,4-dioxo-1-cyclobutene compounds described in the '342 patent generally follows Scheme I (which exemplifies the preparation of 2-Hydroxy-N,N-dimethyl-3-[[2-[[1(R)-(5-methyl-2-furanyl)propyl]amino]-3,4-dioxo-1-cyclobuten-1-yl]amino]benzamide, the compound of Formula I).

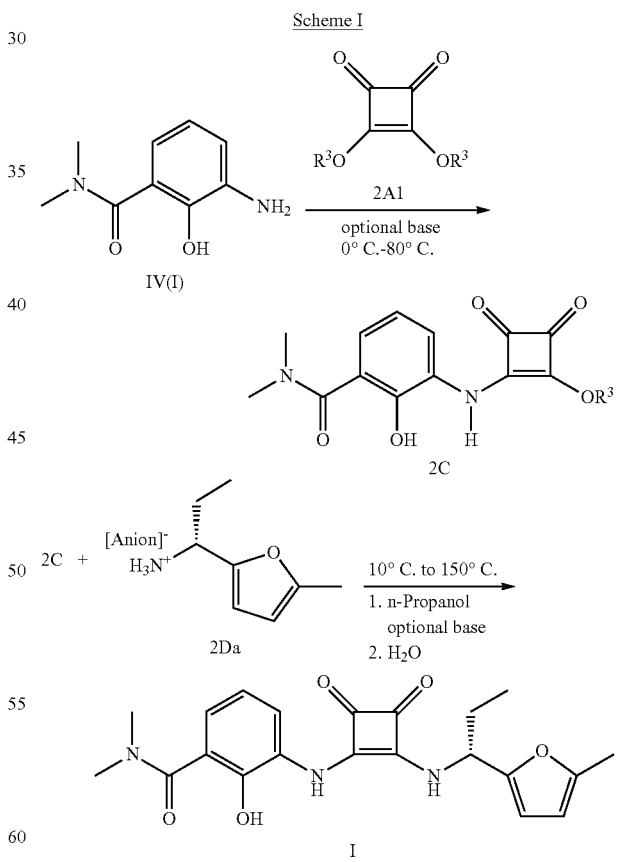

Scheme I

The process for the preparation of the compound of Formula I shown in Scheme I is carried out by first preparing intermediate compound 2C from a dialkyl squarate, a strong skin sensitizer and irritant which is difficult to handle. Additionally, the conditions described in the aforementioned publications under which compounds 2C and 2Da are coupled in the second step of Scheme I produce an undesirable level of impurities admixed with the final product.

Moreover, the process for the preparation of the compound of Formula I shown in Scheme I requires in the first step a reaction between squarate compound 2A1 and intermediate compound IV(i), a 3-amino-2-hydroxy-benzamide compound which is unstable. The stability of the compound of Formula IV(i) makes it difficult to handle, store, and ship. Accordingly, this makes impracticable a process in which the compound of Formula IV(i) is made remotely from the process for making the compound of Formula 2C, or in which the process of making the compound of Formula 2C is not carried out contemporaneously with the preparation of the compound of Formula IV(i). Additionally, the product of Formula 2C provided using commercially available dialkylsquarate has a relatively large amount of impurities necessitating a product purification step prior to utilization in a synthesis of a compound of Formula Ia.

Additionally, as shown in step II of Scheme I, the compound of Formula I shown is prepared from coupling an aminofuran intermediate of Formula 2Da with intermediate compound 2C. The preparation of intermediate compound 2Da is described in U.S. Pat. No. 7,071,342 (the '342 patent) in cols. 35, line 1 to 39, line 20. The '342 patent describes a six step process for preparing the compound of Formula 2DA starting with the commercially available compound of Formula III. In the course of carrying out this process several changes of solvent are required, which leads to diminished isolated yields in the individual steps.

Formula III

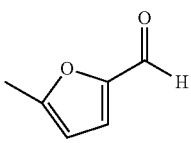

OBJECTIVES AND SUMMARY OF THE INVENTION

In view of the foregoing, what is needed are synthetic processes for the preparation of intermediate 2C and the aminofuran salt intermediate of Formula 2Da having fewer steps and which can be carried out with starting materials that are easier to handle and obtain. What is needed also is a reaction scheme which can provide intermediates 2C and 2Da in a "one-pot reaction"

Additionally, what is needed is a process for preparing 1,2-substituted 3,4-dioxo-1-cyclobutene compounds using the intermediate compound of Formula IV(i) in which the compound of Formula IV(i) can be prepared in a physical location remote from the site in which the other process steps are carried out. Moreover, what is needed is a process which enables the preparation of 1,2-substituted 3,4-dioxo-1-cyclobutene compounds using a source of the compound of Formula IV(i) without a requirement that the source compound be utilized contemporaneously with its initial formation. What is needed also is a reaction scheme utilizing a source of the compound of Formula IV(i) in the preparation of 1,2-substituted 3,4-dioxo-1-cyclobutene compounds which affords practical scale up to a batch size suitable for commercial scale preparation, provides a product with less impurities, and better utilizes dialkylsquarate. What is needed also is a reaction scheme which affords practical scale up to a batch size suitable for commercial scale preparation of 1,2-substituted 3,4-dioxo-1-cyclobutene compounds.

These and other objectives are advantageously provided by the present invention, which in one aspect is a process for preparing 1,2-disubstituted-3,4-dioxo-1-cyclobutene compounds of Formula Ia in accordance with Scheme II.

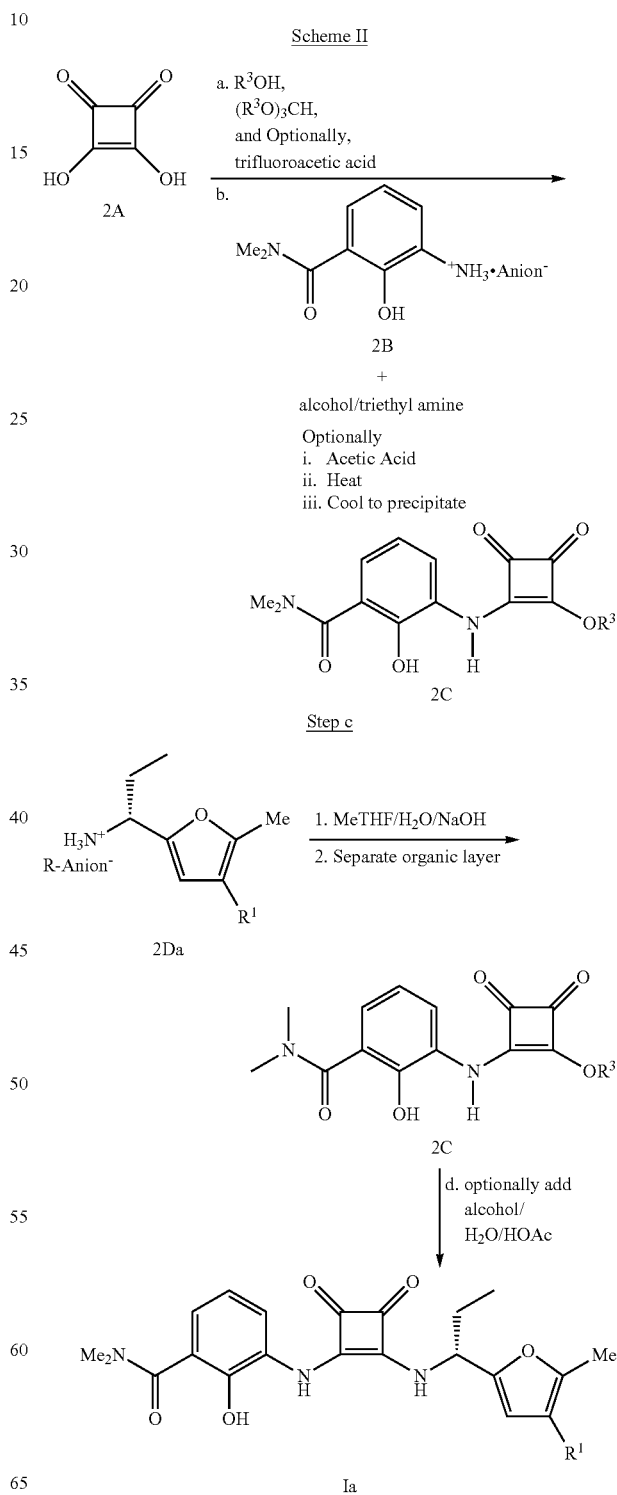

The process of Scheme II comprises:

(a) forming dialkyl-squarate in situ (compound "2A1" of scheme I) by reacting $(R^3O)_3CH$ (trialkylorthoformate) with squaric acid (2A), wherein $R^3$ is a linear or branched alkyl of 6 carbon atoms or less;

(b) reacting amino-hydroxybenzamide compound 2B with the dialkylsquarate formed in step "a" to form compound 2C;

(c) forming in situ a free base amino-furan from the amino-furan salt compound of the formula 2Da wherein, $R^1$ is selected from hydrogen and a substituent comprising from 1 carbon atom to about 10 carbon atoms selected from linear, branched, and cyclic alkyl moieties and substituted linear, branched, and cyclic alkyl moieties and "R-Anion" represents a monovalent anionic moiety, and reacting said free base amino-furan compound with compound 2C formed in step "b" to provide the compound of Formula Ia; and (d) optionally precipitating the compound of Formula Ia by:

(i) successive cycles of concentrating the reaction mixture formed in step "c" by distillation followed by the addition of an aliquot of an alcohol, preferably, when $R^1$ is H, the alcohol is n-propanol and preferably, when $R^1$ is isopropyl, the alcohol is isopropanol;

(ii) adding an aliquot of the alcohol used in step "i" and acetic acid to the concentrate formed in step "i";

(iii) heating the solution formed in step "ii";

(iv) adding an aliquot of water and seed crystals comprising the compound of Formula Ia to the hot solution from step "iii";

(v) cycling the temperature of the seeded solution prepared in step "iv" until a slurry comprising crystals of a desired size is formed; and (vi) optionally isolating the crystals from the slurry prepared in step "v".

In some embodiments of the inventive process it is preferred to carry out step "a", formation of dialkylsquarate from squaric acid, in the presence of an additional acid, preferably trifluoroacetic acid.

In some embodiments of the inventive process it is preferred to carry out step "a", the in situ formation of dialkyl squarate using triethylorthoformate $((CH_3CH_2O)_3CH)$, thus the compound of 2A1 formed is diethyl squarate, the compound of Formula 2A3.

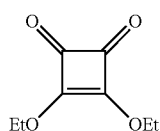

2A3

In some embodiments of the inventive process it is preferred to carry out step "a", the in situ formation of dialkyl squarate using trimethylorthoformate $((CH_3O)_3CH)$, thus the compound of 2A1 formed is dimethyl squarate, the compound of Formula 2A2.

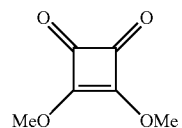

2A2

In some embodiments of the invention in which dimethyl squarate is prepared in situ, it is preferred to carry out the formation of dimethyl squarate in a refluxing alcohol of the Structure $R^3OH$, wherein $R^3$ is a linear or branched alkyl moiety of 6 carbon atoms or less, more preferably $R^3$ is $H_3C$—, thus $R^3OH$ is methanol. In some embodiments, with reference to Scheme II, Step "a", it is preferred to select the $R^3$ substituent in both the trialkylorthoformate reagent (structure $(R^3O)_3CH$) and the alcohol in which the reaction is carried out (structure $R^3OH$) to be the same. Thus, if the trialkylorthoformate reagent is trimethylorthoformate $((H_3CO)_3CH)$, the reaction solvent will be methanol. In some embodiments of the invention in which dimethyl squarate is prepared in situ, it is preferred to concentrate the reaction mixture following the formation of dimethyl squarate prior to reacting with the compound of Formula 2B in subsequent step "b". In some embodiments, subsequent Step "b" preferably uses methanol as the alcohol in which triethylamine is dissolved.

In some embodiments of the inventive process, in Step "c" it is preferred for $R^1$ in the compound amino-furan salt compound of Formula 2Da to be hydrogen or an isopropyl moiety, more preferably, $R^1$ is hydrogen, thus the compound of Formula Ia is a compound of Formula I. In some embodiments, preferably the anion represented by "R-Anion⁻" in the compound of Formula 2Da is a monobasic D-tartarate anion $(HOC(O)[CH_2(OH)]_2C(O)O^-)$ or tartaric acid derivative anion.

In some embodiments of the invention, preferably the compound of Formula 2Da is the compound of formula 2D,

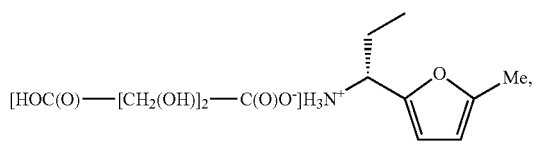

2D thus, with reference to the compound of Formula 2Da, "anion⁻" is a monobasic tartarate anion and $R^1$ is hydrogen.

In some embodiments it is preferred to carry out step "b" of the process (formation of the compound of Formula 2C) at a temperature of from about (−5° C.) to about (+5° C.) and to add triethylamine to the reaction mixture over a portion of the reaction period. In some embodiments it is preferred to seed the reaction mixture used to prepare the compound of Formula 2C with aliquots of solid 2C during the reaction period. In some embodiments it is preferred to work up the reaction mixture of step "b" of the inventive process (preparation of the compound of formula 2C) by heating the reaction mixture with acetic acid and then cooling the reaction mixture to precipitate solid 2C.

In some embodiments of the inventive process, it is preferred to carry out step "c" (formation of the compound of Formula I by reacting compound 2C with the free base formed in situ from compound 2Da) by heating the reaction mixture to reflux and refluxing for a period of time, concentrating the reaction mixture by distillation, and then reflux the concentrated reaction mixture for a second period of time.

In some embodiments it is preferred to carry out optional step "d" of the inventive reaction by adding an aliquot of an alcohol which is i-propanol or n-propanol, concentrating the reaction mixture by distillation, adding a second aliquot of alcohol, concentrating the mixture a second time by distillation, adding a third aliquot of alcohol and acetic acid, filtering the reaction mixture, adding additional alcohol and heating the mixture, then adding water, seeding the mixture with crystals of the compound of Formula I and cooling the mixture. In some embodiments, the mixture is cycled between ambient temperature and a temperature of from about 45° C. to about 60° C. until crystals of desired size are formed.

Another aspect of the present invention is a process for the preparation of intermediate compound (2Ca) useful in the provision of compounds of Formula Ia, (b) reacting the amino-hydroxide benzamide salt compound of Formula 2B,

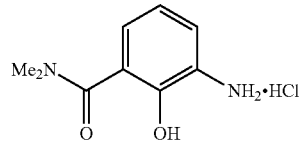

Formula 2B with the dimethylsquarate formed in step "a" to form compound 2Ca.;

In some embodiments forming intermediate compound (2Ca) it is preferred to carry out step "a" of the process in methanol. In some embodiments for the preparation of compound (2Ca) it is preferred to perform an optional isolation step in which the reaction mixture containing the compound of Formula (2Ca) is worked up by adding acetic acid, heating the reaction for a period of time, seeding the reaction mixture with a solid form of the compound of Formula (2Ca), and cooling the resulting mixture to precipitate a solid form of product (2Ca).

In another aspect, the present invention provides a process for preparing carbamoyl benzamine salts of Formula 2B1 in accordance with Scheme III, which illustrates also the optional conversion of the compound of Formula 2B1 into squarate intermediates of Formula 2C.

Scheme III

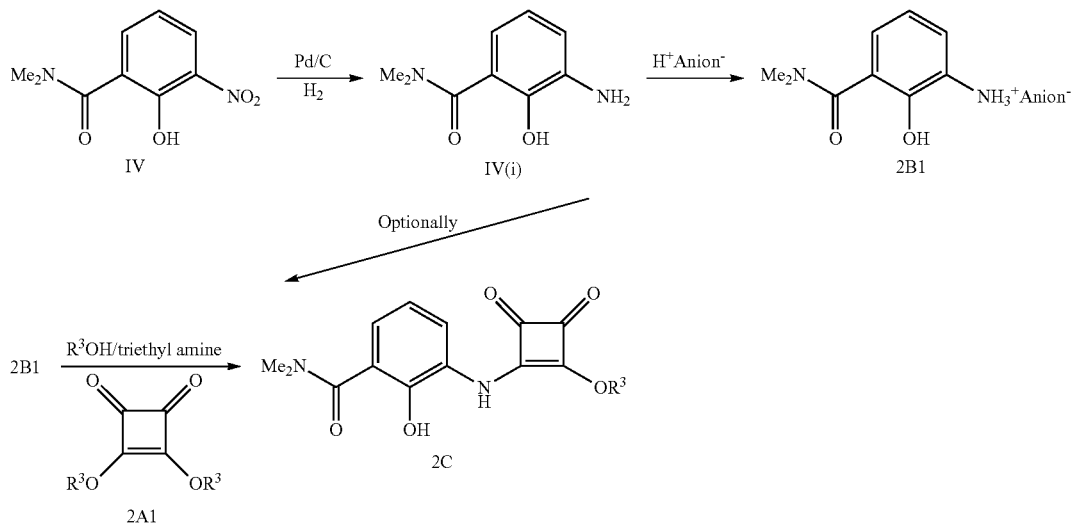

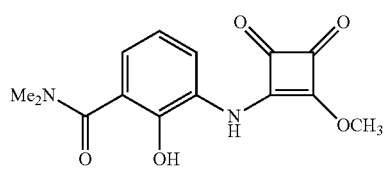

Formula 2Ca the process comprising:
(a) forming dimethyl-squarate in situ by reacting $(CH_3O)_3CH$ with squaric acid and optionally additionally trifluoroacetic acid; and The process of Scheme III comprises:
(a) providing a 3-amino-2-hydroxy-N,N-dimethyl-benzamide compound of Formula IV(i)) and subsequently reacting it with an acid of the Formula $H^+Anion^-$, wherein "$Anion^-$" is a monovalent anionic moiety, to form the compound of Formula 2B1;
(b) optionally, precipitating the compound of Formula 2B1 and collecting the precipitate; and
(c) optionally reacting the compound of Formula 2B1 with a dialkyl squarate compound of Formula 2A1 to form the compound of Formula 2C.

In some embodiments of the inventive process it is preferred to carry out the reaction of step "a", formation of the salt compound of Formula 2B1, in a mixed solvent comprising methyl tertiarybutyl ether (MTBE) and ethanol. In some embodiments it is preferred to carry out reaction step "a" using an acid selected from mineral acids, for example, but not limited to $H_2SO_4$, $H_3PO_4$, HBr, and HCl, and organic acids, for example, but not limited to, maleic acid, fumaric acid, malic acid, sulfonic acids, oxalic acid, and tartaric acids and derivatives thereof. When a mineral acid is used, preferably the acid is HCl (thus "A$^-$" is Cl$^-$). When an organic acid is used, preferably the acid is selected from p-tolysulfonic acid (thus "A$^-$" is p-tolysulfonate), oxalic acid (thus "A$^-$" is oxalate), and tartaric acid (thus "A$^-$" is monobasic tartarate (HO—C(O)—(HOCH)$_2$C(O)O$^-$), more preferably tartaric acid acid is used. In some embodiments it is preferred to use a concentrated aqueous acid solution to carry out reaction step "a". In some embodiments it is preferred to carry out step "a" by treating the reaction mixture containing the compound of Formula IV with a solid acid.

In some embodiments, step "c", the preparation of the compound of the Formula 2C, additionally includes the steps of seeding the reaction mixture with a solid form of the compound of Formula 2C, heating the reaction mixture in the presence of acetic acid and cooling the reaction mixture to precipitate a solid form of the compound of Formula 2C. In some embodiments of the invention it is preferred to seed the reaction mixture provided in step "a" with a solid portion of the compound of Formula 2B1 selected from compound 2B1 prepared in accordance with the '342 patent and compound 2B1 sourced from an earlier batch of material prepared in accordance with the process of the present invention.

In some embodiments of the invention it is preferred to carry out step "a" of the process in a place and time remote from carrying out step "b" of the process. In some embodiments of the invention it is preferred to precipitate and collect a solid form of the compound of the Formula of 2B1 prepared in step "a" and store it for later use in carrying out step "b" of the process.

In some embodiments of the process it is preferred to provide the compound of Formula VI(i) in accordance with Scheme IIIa.

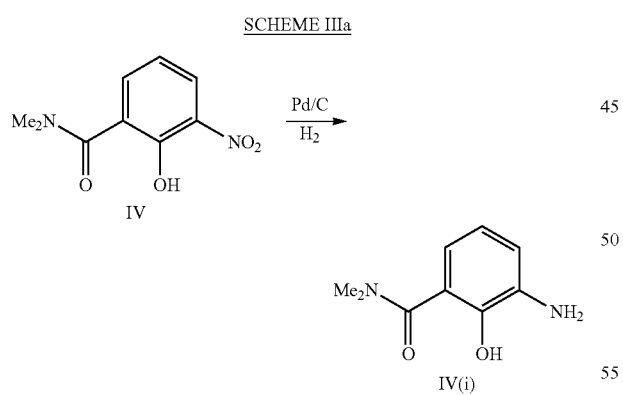

Thus, the compound of Formula IV(i) is provided by reducing the compound of Formula IV using a hydrogenation catalyst, preferably a palladium catalyst, more preferably palladium on carbon black. In some embodiments it is preferred to use the reaction mixture produced after the reduction of the compound of Formula IV as a source of the compound of Formula VI(i) in the preparation of the compound of Formula 2B1.

In another aspect, the present invention provides compounds of Formula Ia in accordance with the process of Scheme II, wherein, in Step "c" of the process, the salt compound of Formula 2Da (from which the corresponding freebase amino-furan is prepared) is itself provided by the process of Scheme IV:

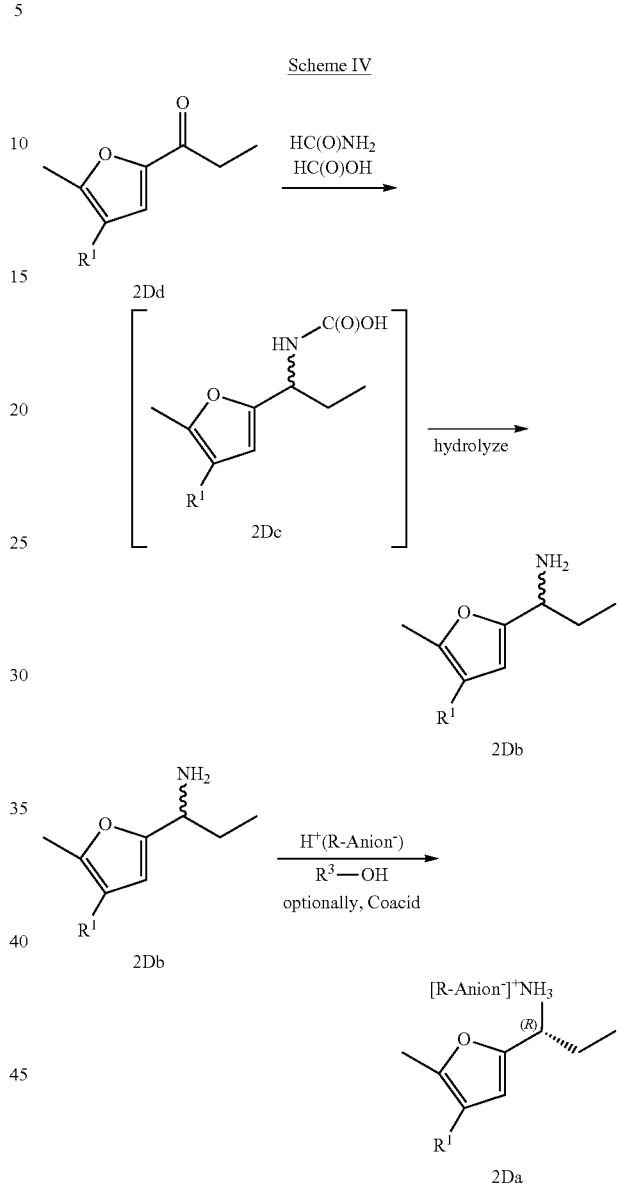

the process comprising:
a. reductively aminating the compound of Formula (2Dd) by treatment with formamide in the presence of formic acid to provide the intermediate compound (2Dc), preferably. $R^1$ is hydrogen or a substituent comprising from 1 carbon atom to about 10 carbon atoms selected from linear, branched, and cyclic alkyl moieties and substituted linear, branched, and cyclic alkyl moieties;
b. hydrolyzing, preferably in situ, the compound of Formula (2Dc) prepared in Step "a", preferably by the addition of aqueous base to the reaction mixture, yielding the freebase racemic mixture of Formula (2Db); and
c. treating the reaction mixture comprising the freebase racemate (2Db) with an acid of the formula H$^+$[R-Anion$^-$] in the presence of an alcohol of the formula R$^3$OH, and optionally in the presence of a coacid, wherein "R-Anion" represents an optically active monovalent anionic moiety, preferably capable of preferentially forming a salt of the R-isomer of the compound of Formula 2D, and R³ is selected from linear, branched, and cyclic alkyl of 6 carbon atoms or less, thereby yielding a salt of the desired isomer.

In some embodiments of the process of Scheme IV it is preferred for R¹ in the compounds of the Formulae (2Da) through (2Dd) to be hydrogen or isopropyl. In some embodiments, it is preferred for the alcohol of Formula R³OH in step "c" to be methanol or ethanol. In some embodiments using a coacid in resolution step "c", the coacid is preferably HCl, malonic acid, acetic acid, formic acid, chloroacetic acid, or trifluoroacetic acid, or mixtures thereof, more preferably, the coacid is trifluoroacetic acid.

In some embodiments of the process of Scheme IV it is preferred to carry out Step "a", using 5-methyl-2-propionyl-furan as the compound of Formula 2Dd (thus R¹ is hydrogen).

In some embodiments of the inventive process, R¹ in the amino-furan salt compound of Formula 2Da is hydrogen (thus providing the compound of Formula I) or an isopropyl moiety (thus providing the compound of Formula II). In some embodiments, preferably, the anion represented by "R-Anion⁻" in the compound of Formula 2Da is an optically active monovalent anionic moiety capable of preferentially forming a salt of the R-isomer of the compound of Formula 2D. Examples of suitable anions include, but are not limited to, monobasic D-tartarate anion (HOC(O)[CH₂(OH)]₂C(O)O⁻) and tartarate anion derivatives, for example DDTA.

In some embodiments of the invention, the compound of Formula 2Da is preferably the compound of formula 2Da1,

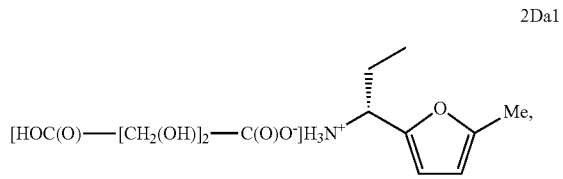

2Da1

(thus, "Anion" in the compound of Formula 2Da is a monobasic tartarate anion and R¹ is hydrogen).

In some embodiments of the inventive process illustrated in Scheme IV step "c" (formation of the compound of Formula I by reacting compound 2C with the free base formed in situ from compound 2Da) is preferably carried out by heating the reaction mixture to reflux and refluxing the reaction mixture for a period of time, concentrating the reaction mixture by distillation, and then refluxing the concentrated reaction mixture for a second period of time.

In some embodiments it is preferred to carry out optional step "d" of the inventive process illustrated in Scheme IV by adding an aliquot of n-propanol, concentrating the reaction mixture by distillation, adding a second aliquot of n-propanol, concentrating the mixture a second time by distillation, adding a third aliquot of n-propanol and acetic acid, filtering the reaction mixture, adding additional n-propanol and heating the mixture, then adding water, seeding the mixture with crystals of the compound of Formula I and cooling the mixture. In some embodiments, the mixture is cycled between ambient temperature and a temperature of from about 55° C. to about 70° C. until crystals of desired size are formed.

Other aspects and advantages of the invention will become apparent from following Detailed Description.

DETAILED DESCRIPTION OF THE INVENTION

Terms used in the general schemes herein, in the examples, and throughout the specification, include the following abbreviations, together with their meaning, unless defined otherwise at the point of their use hereinafter: Me (methyl); Bu (butyl); t-Bu (tertiary butyl); Et (ethyl); Ac (acetyl); t-Boc or t-BOC (t-butoxycarbonyl); DMF (dimethylformamide); THF (tetrahydrofuran); DIPEA (diisopropylethylamine); MTBE (methyltertiarybutyl ether); 2-Me-THF (2-methyl tetrahydrofuran

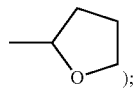

n-propyl, n-prop (CH₃CH₂CH₂—); RT (room temperature, ambient temperature, generally 25° C.); TFA (trifluoroacetic acid); TEA (triethyl amine), i-propanol means isopropanol, n-propanol means normal propyl alcohol.

As used herein, the following terms, unless otherwise indicated, are understood to have the following meanings:

The term "substituted" means that one or more hydrogens on the designated atom or group of atoms in a structure is replaced with a selection from the indicated group, provided that the designated atom's normal valency under the existing circumstances is not exceeded, and that the substitution results in a stable compound. Combinations of substituents and/or variables are indicated when such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

"Patient" includes both humans and animals.

"Mammal" means humans and other mammalian animals.

"Alkyl" means an aliphatic hydrocarbon group which may be linear straight or branched and comprising about 1 to about 10 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

"Alkenyl" means an aliphatic hydrocarbon group containing at least one carbon-carbon double bond and which may be straight or branched and comprising about 2 to about 10 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methylbut-2-enyl and n-pentenyl.

"Alkylene" means a difunctional group obtained by removal of an additional hydrogen atom from an alkyl group, as "alkyl" is defined above. Non-limiting examples of alkylene include methylene (i.e., —CH₂—), ethylene (i.e., —CH₂—CH₂—) and branched chains, for example, —CH(CH₃)—CH₂—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Cycloalkyl" means a non-aromatic mono- or multicyclic ring system comprising about 3 to about 10 carbon atoms, preferably about 3 to about 6 carbon atoms. Non-limiting examples of suitable monocyclic cycloalkyls include cyclopropyl, cyclobutyl, cyclopentyl, cyclohexyl, cycloheptyl and the like. Non-limiting examples of multicyclic cycloalkyls include, but are not limited to 1-decalin, norbornyl and cognitors, adamantyl and cognitors.

"Halo" means a halogen selected from fluoro, chloro, bromo, or iodo groups.

"Aminoalkyl" means an alkyl as defined above having at least one hydrogen atom on the alkyl moiety replaced by an amino functional (i.e., —NH$_2$) group. Alkylamino means an amino functional group having one or both hydrogens replaced by an alkyl functional group, as "alkyl" is defined above.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

A wavy line ~~~ appearing on a structure and joining a functional group to the structure in the position of a bond generally indicates a mixture of, or either of, the possible isomers, e.g., containing (R)- and (S)-stereochemistry. For example,

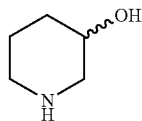

means containing either, or both of

A wavy line which terminates a bond indicates that the portion of the structure depicted is attached to a larger structure at the indicated bond, for example,

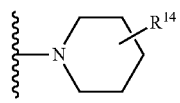

implies that the nitrogen of the substituted piperidyl group depicted is bonded to an undepicted structure on which it is a substituent.

Lines drawn into ring systems, for example the substituted aryl group:

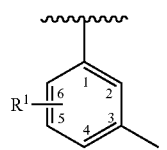

indicates that a substituent ($R^1$) may replace a hydrogen atom of any of the ring carbons otherwise bonded to a hydrogen atom. Thus, as illustrated, $R^1$ can be bonded to any of carbon atoms 2, 4, 5, or 6, but not 3, which is bonded to a methyl substituent, or 1, through which the substituted aryl group is bonded.

As well known in the art, a bond drawn from a particular atom wherein no moiety is depicted at the terminal end of the bond indicates a methyl group bound through that bond to the atom, unless stated otherwise. For example:

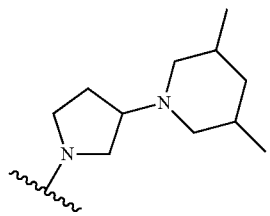 [SMILES: *N1CCC(N2CC(C)CC(C)C2)C1]

represents

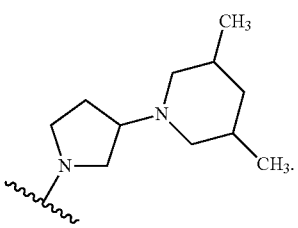 [SMILES: *N1CCC(N2CC(C)CC(C)C2)C1]

However, in some structures shown herein, the CH$_3$ moiety is explicitly included in a structure. Herein, the use of either convention for depicting methyl groups is meant to be equivalent and these conventions are used herein interchangeably for convenience and without intending to alter thereby the meaning which is conventionally understood using either depiction.

The term "isolated" or "in isolated form" for a compound refers to the physical state of said compound after being isolated from a process. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

When any variable (e.g., aryl, heterocycle, $R^2$, etc.) occurs more than one time in any constituent or in a formula, its definition on each occurrence is independent of its definition at every other occurrence.

As mentioned above, a process for preparing each of the compounds of Formula I and Formula II have been described U.S. Pat. No. 7,123,455 (the '455 patent, both compounds) and U.S. Pat. No. 7,071,342 (the '342 patent, the compound of Formula I). The present invention utilizes the processes depicted in Schemes I, II, II(a and b) and IV to prepare the compounds of Formula Ia, for example, the compounds of Formulae I and II. Aspects of the preparation and purification of the compounds of Formulae I and II are also discussed in U.S. provisional application Ser. Nos. 60/958,313, 60/958, 317, and 60/958,311, each of which was filed on Jul. 3, 2007, and the disclosure of each of which is incorporated herein by reference in its entirety.

Scheme V presents a coupling reaction between a salt of an amino-furate (2Da) and an amino-substituted hydroxyl-benzamide (2C) which is carried out in 2-methyl-tetrahydrofuran (2-MeTHF) and the product is optionally extracted into isopropyl alcohol, and wherein, optionally, the freebase aminofuran intermediate is generated from the corresponding salt.

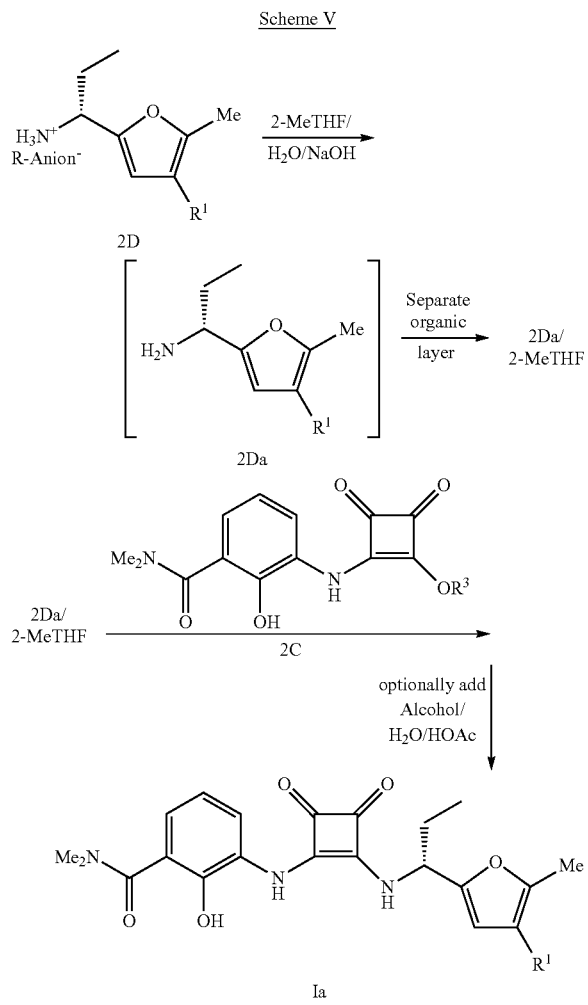

Scheme V

The coupling reaction depicted in Scheme V is a process comprising:
- (a) forming a free base amino-furan compound 2Da from the amino-furan salt compound of the formula 2D wherein, $R^1$ is selected from hydrogen and a substituent comprising from 1 carbon atom to about 10 carbon atoms selected from linear, branched, and cyclic alkyl moieties and substituted linear, branched, and cyclic alkyl moieties and "A-Anion" represents a monovalent anionic moiety which is preferably an optically active monovalent anionic moiety capable of preferentially forming a salt of the R-isomer of the compound of Formula 2D;
- (b) reacting said free base amino-furan compound 2Da with a hydroxyaminobenzamide compound of Formula 2C to provide the compound of Formula Ia; and
- (c) optionally precipitating the compound of Formula Ia by:
  - (i) successive cycles of concentrating the reaction mixture formed in step "c" by distillation followed by the addition of an aliquot of an alcohol;
  - (ii) adding an aliquot of acetic acid and the alcohol used in Step "i" to the concentrate formed in step "i";
  - (iii) heating the solution formed in step "ii";
  - (iv) adding an aliquot of water and seed crystals comprising the compound of Formula Ia to the hot solution from step "iii";
  - (v) cycling the temperature of the seeded solution prepared in step "iv" until a slurry comprising crystals of a desired size is formed; and
  - (vi) optionally isolating the crystals from the slurry prepared in step "v".

Although Step "a" of Scheme V can be carried out in a various solvents, the inventors have surprisingly found that the coupling reaction between the hydroxyamino-benzamide and aminofuran shown in Step "a" occurs with an improved impurity profile if the coupling reaction is conducted in a solvent of 2-methyltetrahydrofuran. Conveniently, the aminofuran used in the coupling reaction shown in Scheme V can be provided by liberating the free base form of the aminofuran to be reacted from its corresponding salt. Accordingly, the aminofuran salt can be prepared at a time and place remote from the synthesis of a compound of Formula I, and shipped or stored for use as desired in providing the freebase aminofuran precursor used in the preparation of a compound of Formula I. It will be appreciated that Step "a" of Scheme V can be carried out using any amino-furan salt, for example, where "R-Anion⁻" is any monovalent ionic moiety, for example, but not limited to the anion from a mineral acid, for example, $H_2SO_4$, $H_3PO_4$, HBr, and HCl, and the anion from an organic acid, for example, but not limited to, maleic acid, fumaric acid, malic acid, sulfonic acids, oxalic acid, and tartaric acids and derivatives thereof. However, preferably, the compound of Formula 2D comprises an "R-Anion⁻" where "R-Anion⁻" is a monovalent anion which preferentially forms a salt with the R-isomer of the aminofuran, for example, but not limited, to monovalent D-tartarate ion. Conveniently, in selecting a salt made with an "R-Anion⁻" which preferentially forms a salt with the R-isomer of the amino-furan, an aminofuran salt useful in the inventive process can be precipitated from a mixture of isomers without the need for complex procedures to isolate the desired isomer prior to forming the salt.

Thus, as shown in Step "a" of Scheme V, a 2-methyltetrahydrofuran solution of the aminofuran free base is provided by treatment of a 2-methyl-tetrahydrofuran suspension of the corresponding salt with a strong aqueous base. Upon reaction with the aqueous base, the freebase form of the aminofuran is liberated and dissolves in the 2-methyltetrahydrofuran in which the precursor salt was suspended. The organic layer of the reaction mixture is then easily obtained in isolation from the reaction mixture using physical means, for example, separation and decantation. The hydroxyaminobenzamide (2C) to be coupled with the aminofuran is added to the 2-methyltetrahydrofuran solution containing the aminofuran freebase, and heated to initiate the coupling reaction. The reaction can be carried out at temperatures above 0° C., preferably a temperature of at least 40° C., and more preferably the reaction is carried out at a temperature of about 70° C.

In some embodiments it is preferred to select hydroxyaminobenzamide (compound of Formula 2C) as the limiting reagent. In some embodiments, preferably after a substantial portion of the limiting reagent has been consumed, aliquots of an alcohol which is normal propanol or isopropanol are added to the reaction mixture with subsequent distillation to concentrate the reaction mixture. In some embodiments it is preferred to carry out several cycles of adding the alcohol and subsequently distilling volatiles from the reaction mixture until the reaction mixture comprises substantially the added alcohol, thus facilitating the separation of the product compound of Formula Ia from the reaction mixture by crystallization. In some embodiments, when $R^1$ of the compound of Formula Ia is hydrogen, preferably n-propanol is employed, and when $R^1$ of the compound of Formula Ia is an isopropyl substituent, preferably the alcohol is isopropanol. To this end a final aliquot of the selected alcohol and a small amount of acetic acid is added to neutralize any residual base, thereby maximizing yield. The mixture is subsequently filtered and the filtrate is diluted with additional alcohol and heated to at least 70° C. Water is added to the heated mixture as an antisolvent while maintaining the temperature. The mixture is then cooled to about 60° C. and seed crystals of the compound of Formula Ia are added and the mixture is subjected to controlled cooling to facilitate crystallization of the compound of Formula Ia.

The inventors have found that in some embodiments, for example, when the compound of Formula Ia is the compound of Formula I, cycling the temperature of the seeded mixture between ambient temperature and a temperature of from about 50° C. to about 60° C. permits control of the size of the crystals formed.

For use in carrying out the synthesis shown in Scheme V, above, the aminohydroxybenzamide intermediate compounds of Formula 2C are conveniently prepared by reacting a dialkyl squarate, for example, dimethyl squarate and diethyl squarate, preferably, dimethyl squarate, and the compound of 2B in accordance with Scheme VI, shown below.

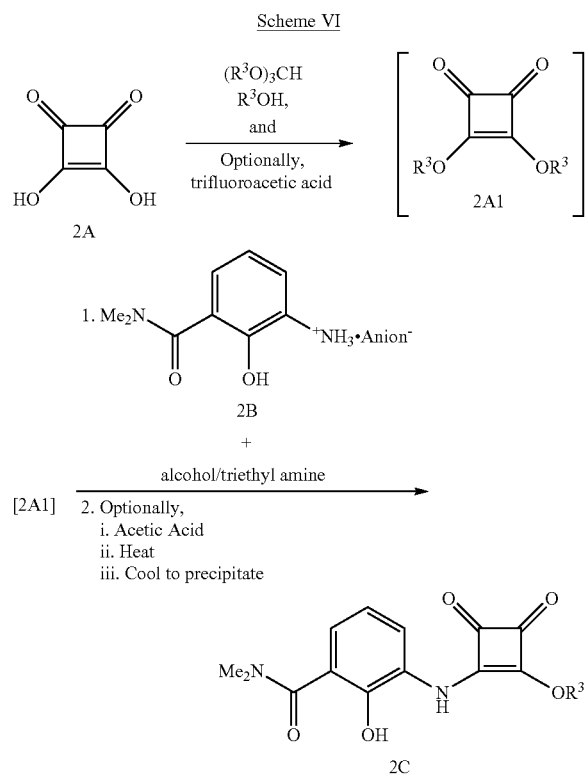

Scheme VI illustrates a process comprising:
(a) forming dialkyl-squarate compounds of Formula 2A1 in situ by reacting $(R^3O)_3CH$ (trialkylorthoformate) with squaric acid (2A), wherein $R^3$ is a linear or branched alkyl of 6 carbon atoms or less; and (b) reacting the compound of Formula 2A1 prepared in step "a" with a salt of a 2-hydroxy-2-amino-benzamide compound of Formula 2B, wherein [Anion⁻] is a monovalent anionic moiety defined below.

Surprisingly, the inventors have found that the coupling reaction shown in Scheme VI can be carried out by generating the dialkyl squarate in situ from a reaction between squaric acid (compound 2A) and a trialkylorthoformate $[(R^3O)_3CH]$. Preferably the trialkylorthoformate is selected from trimethyl orthoformate and triethylorthoformate, more preferably trimethylorthoformate. In some embodiments it is preferred to use a slight excess of trialkylorthoformate in comparison to the amount of squaric acid employed. In some embodiments it is preferred to use about 1 equivalent of squaric acid and about 2.1 equivalents of trialkylorthoformate.

Optionally, the esterification reaction providing dialkyl squarate of Formula 2A1 is catalyzed with a small amount of acid, preferably trifluoroacetic acid. In some embodiments of the inventive process using trifluoroacetic acid to catalyze the reaction between trimethylorthoformate and squaric acid it is preferred to use about 1 mole % of trifluoroacetic acid relative to the amount of trimethylorthoformate employed.

Squaric acid is an article of commerce available, for example, from Aldrich. The inventors have surprisingly found that generating dialkylsquarate (2A1) in situ from squaric acid (2A) permits the process to be run without requiring isolation and handling a dialkyl squarate in the preparation of the intermediate compound (2C). Dialkylsquarates are known to be irritants and skin sensitizers. By generating the dialkylsquarate in situ for use in preparing intermediate 2C the present process eliminates the necessity of handling dialkyl squarate and thereby improves the safety and scalability of the process.

Any trialkyl orthoformate of the formula $[(R^3O)_3CH]$, wherein $R^3$ is linear or branched alkyl having 6 carbon atoms or less is suitable for carrying out step 1 of dialkylsquarate synthesis reaction shown in Scheme VI, preferably, the trialkylorthoformate is triethylorthoformate (yielding diethyl squarate as the compound of Formula 2A1) or trimethyl orthoformate (yielding dimethyl squarate as the compound of Formula 2A1), more preferably the reaction is carried out with trimethyl orthoformate. It will be appreciated that other methods of generating dialkylsquarates in situ can also be employed without departing from the scope of the present inventive reaction.

In some embodiments, Scheme VI, Step "a", in situ generation of dialkyl squarate, is preferably carried out in a refluxing alcohol having the structure $(R^3OH)$, wherein "—$R^3$" is selected to be the same as the alkyl moiety present in the trialkylorthoformate $[(R^3O)_3CH]$ used in the provision of dialkyl squarate from squaric acid. Thus, for example, when diethyl squarate is prepared (by reaction with triethylorthoformate) the reaction is preferably carried out in ethanol. When dimethyl squarate is prepared (by reaction with trimethylorthoformate) the reaction is preferably carried out in methanol. In some embodiments it is preferred to prepare dimethylsquarate by reacting squaric acid with trimethylorthoformate in methanol. In some embodiments, at the end of the refluxing period for preparing a dialkylsquarate, it is preferred to concentrate the reaction mixture by distilling volatiles from the reaction mixture. In some embodiments using methanol as the reaction solvent, it is preferred to concentrate the solution containing the dialkylsquarate prepared in situ by refluxing the reaction mixture until it reaches a temperature of about 70° C. and to distill off volatiles while maintaining the temperature at about 70° C. until distillation ceases.

After obtaining an alcohol solution of dialkylsquarate (preferably a methanol solution of dimethyl squarate) in accordance with Step "a" of Scheme VI, the solution can be employed directly in Step "b" of Scheme VI, (the formation of the compound of Formula 2C). In some embodiments of the process shown in Scheme VI it is preferred to concentrate the alcohol solution comprising dialkylsquarate obtained in Step "a" prior to using it in Step "b". In some embodiments of the process illustrated in Scheme VI the concentrated the alcohol solution comprising dialkylsquarate from Step "a" is diluted by adding additional amounts of the alcohol solvent before it is used in Step "b" of the process. In some embodiments it is preferred to dilute the concentrated solution of dialkylsquarate from Step "a" to 6× the volume by adding additional aliquots of the same alcohol comprising the concentrated solution of dialkylsquarate in preparation to carry out Step "b" of Scheme VI (the coupling reaction forming the compound of the Formula 2C). In some embodiments it is preferred to carry out the coupling reaction at a temperature of mess than about 30° C., more preferably at a temperature of from about [−10° C.] to about [+10° C.], and more preferably at a temperature of from about [−5° C.] to about [+5° C.].

In some embodiments of the process illustrated in Scheme VI, Step "b" is carried out after cooling the solution of dialkyl squarate by adding amino-hydroxybenzamide salt of Formula 2B to the alcoholic solution of dialkylsquarate in an amount that provides from about 0.5 equivalents to about 1.0 equivalents of the benzamide salt in comparison with the dialkylsquarate present in solution, preferably about 0.7 equivalent of the benzamide salt is employed. In some embodiments it is preferred for the salt compound of Formula 2B to be the hydrochloride salt compound of Formula 2B1.

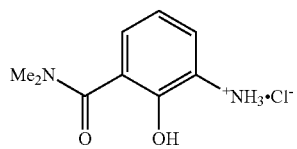

Formula 2B1

In some embodiments it is preferred to mediate the coupling reaction (Scheme VI, Step "b") with an organic base, for example, but not limited to pyridine, pyridine derivatives, and tertiary amines, for example, but not limited to, triethyl amine. Preferably the base is a tertiary amine, more preferably it is selected from diisopropylethylamine and triethyl amine, more preferably the base is triethylamine. When used, it is preferred to employ at least about one equivalents of the base in comparison with the amount of benzamide salt employed, preferably about 1.8 equivalents.

In some embodiments using triethylamine to mediate the coupling reaction, it is preferred to add the triethylamine over a period of the reaction time, preferably about two thirds of the reaction period, while maintaining the reaction mixture temperature from about [−5° C.] to about [+5° C.]. In some embodiments utilizing triethylamine, it is preferred to work up the reaction after the reaction period by seeding the reaction mixture with the solid amounts of the compound of formula 2C to nucleate crystal growth, then add acetic acid to insure that any base still present is neutralized, thus maximizing yields of the coupled product. When used, it is preferable to add an amount of acetic acid equivalent to twice the mole amount of triethylamine added. In some embodiments employing acetic acid, following acid addition it is preferred to heat the reaction mixture, preferably to at least 60° C., more preferably to a temperature of from about 60° C. to about 70° C., then lower the temperature in controlled stages, preferably, first to a temperature of less than about 35° C., more preferably to a temperature of from about 25° C. to about 35° C., followed by a period of time in which the reaction mixture is cooled, preferably to a temperature of from about [−5° C.] to about [+5° C.], to precipitate crystals of the intermediate compound of Formula 2C.

The aminofuran salt compounds of Formula 2D used in the process of Scheme V (above) are preferably prepared in accordance with Scheme VII (below).

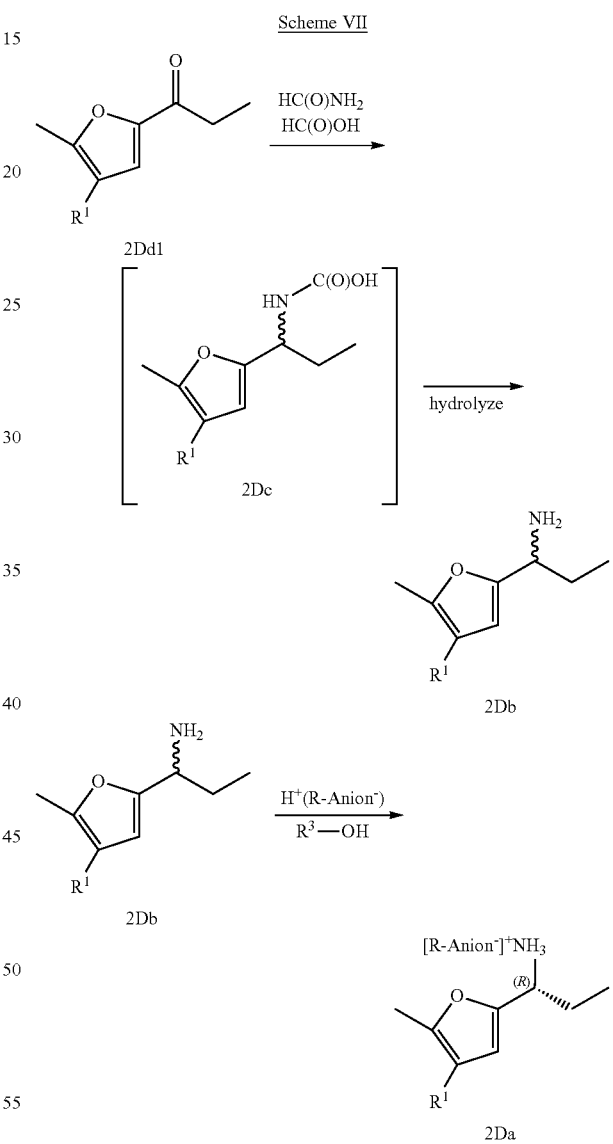

Scheme VII

Scheme VII utilizes as a starting material a 4-substituted-5-methyl-2-propionylfuran (2Dd), wherein $R^1$ is hydrogen or a substituent comprising from 1 carbon atom to about 10 carbon atoms selected from linear, branched, and cyclic alkyl moieties and substituted linear, branched, and cyclic alkyl moieties. The process of Scheme VII comprises reductively aminating the compound of Formula (2Dd) by treatment with formamide in the presence of formic acid to provide an intermediate compound of the Formula (2Dc), hydrolyzing intermediate (2Dc) in situ by the addition of aqueous base to the reaction mixture yielding the freebase racemic compound (2Db); and precipitating a salt form of the compound 2Db by treating it with an acid of the Formula H⁺[R-Anion⁻], wherein "R-Anion⁻" represents a monovalent anionic moiety. Preferably, the acid used to precipitate 2Db comprises an "R-Anion⁻" which is an optically active anionic moiety capable of preferentially forming a salt of the R-isomer of the compound of Formula 2D, thereby resolving the racemic reaction mixture by selective precipitation of the compound of the Formula (2Da). When $R^1$ is an isopropyl substituent ((CH₃)₂CH—), the compound of Formula 2Da is named (R) 1-(4-Isopropyl-5-methyl-furan-2-yl)-propylamine, also termed herein for convenience, (R)-ethyl-5-methyl-2-furanmethanamine. Examples of "R-Anion⁻" which are suitable for resolving the reaction mixture containing the freebase racemate (2Db) according to the foregoing include, but are not limited to, tartaric acid and derivatives thereof. Preferably the acid used for resolving the reaction mixture is dissolved in an alcohol, which is preferably methanol or ethanol.

The inventors have surprisingly found that using the process illustrated in Scheme VII with an optically active "R-Anion⁻" can provide precipitation yields of over 80% of the desired R-isomer present in the racemic solution and yield a precipitate having an optical purity in excess of about 94% ee. In some embodiments it is preferred to add a coacid along with the acid supplying "[R-Anion⁻]" to decrease the amount of the optically active acid needed to achieve resolution of the target compound and may increase the optical purity of the precipitated solids. The inventors have surprisingly found that the use of a coacid can provide an optically active product having more than about 99% ee. In some embodiments using a coacid, the coacid is preferably HCl, malonic acid, acetic acid, formic acid, chloroacetic acid, or trifluoroacetic acid, more preferably the coacid is trifluoroacetic acid.

In some embodiments, optionally, preceding the resolution step in Scheme VII, wherein the desired isomer of the compound of Formula 2Db is precipitated as a salt, the reaction mixture is treated with an acid having an anion which preferentially forms an insoluble complex with the unwanted isomer of the compound of the Formula 2Db, thereby preferentially precipitating the unwanted isomer and increasing the ratio of desired isomer to unwanted isomer in solution. It will be appreciated that when such a step precedes the resolution step shown in Scheme VII, prior to treatment with an optically active acid to precipitate the desired isomer the reaction mixture is filtered to remove precipitate solids comprising the unwanted isomer. Without wanting to be bound by theory, it is believed that in most cases precipitation of the unwanted isomer prior to precipitating the desired isomer will provide an increase in the enantiomeric purity of the product produced in the resolution step.

Preferably, $R^1$ in the compound of Formula (2Dd) is hydrogen or isopropyl (—CH(CH₃)₂). When $R^1$ is hydrogen, the compound of Formula 2Dd is 2-methyl-5-propionyl furan and is commercially available. In some embodiments where $R^1$ is hydrogen, preferably the solvent $R^3$—OH used in the resolution step is methanol. In some embodiments where $R^1$ is isopropyl, preferably solvent $R^3$—OH used in the resolution step is ethanol.

In some embodiments, preferably the process of providing aminofuran salt compound of Formula (2Da) is carried out with the formamide starting compound of Formula (2Dd) dissolved in formamide and add the required amount of formic acid thereto. In some embodiments it is preferred to heat the reaction mixture after the addition of formic acid to a temperature of at least about 100° C., preferably to a temperature of from about 140° C. to about 150° C.

In some embodiments, after reductive amination and hydrolysis, it is preferred to extract the crude racemic aminofuran of Formula (2Db) from the reaction mixture with an alcohol of the Formula $R^3$—OH, and carry out the resolution step "c" using the resulting alcohol solution of crude aminofuran, where $R^3$— is a linear or branched alkyl of 6 carbon atoms or less.

As mentioned above, with reference to Scheme I and Scheme IIIa, the preparation of the compound of Formula IV(i) [3-amino-2-hydroxy-benzamide] and its use in the synthesis of compounds of Formula; is described in U.S. Pat. No. 7,071,342 (the '342 patent), see for example, col. 23, lines 3 to 30.

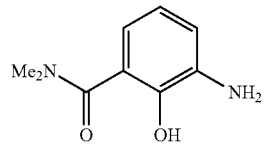

Formula IV(i)

However the inventors have found that the compound of Formula IV(i) is unstable, making isolating, storing, and shipping the free-base compound problematic. Surprisingly, the inventors have found that treatment of the compound of Formula IV(i) with an acid to form the salt compound of Formula 2B (Scheme VI), for example, the compound of Formula 2B1,

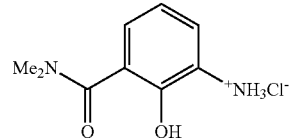

Formula 2B1 yields sufficiently stable intermediate compounds that they can be made remotely, then isolated, shipped and stored for use at a time and in a place which is convenient to carry out further reactions, for example, as illustrated in Scheme VI using the compound of Formula 2B to prepare compounds of Formula Ia. Moreover, with reference to Scheme VI, the inventors have found that the benzamide/dialkyl squarate coupling reaction leading to the compound of Formula 2C proceeds more readily when the benzamide salt of Formula 2B1 is used in the coupling step in place of the compound of Formula IV(i) and the reaction is carried out in a polar solvent in the presence of a tertiary amine base, for example, triethylamine.

In some embodiments the compound of Formula 2B is prepared starting with a compound of Formula IV(i)a,

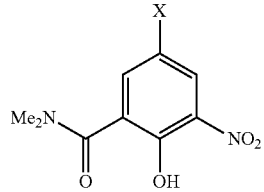

Formula IVa wherein "X" is selected from hydrogen and a halogen selected from F, Cl, Br, and I.

Although it will be appreciated that the compound of Formula 2B1 can be prepared in many different ways, in some embodiments of the present invention process it is preferred to prepare a compound of Formula IV(i) by reducing the compound of Formula IV as shown in step 1 of Scheme III. The preparation of the compound of Formula IV and its reduction to the compound of Formula VI(i) has been described in the '342 patent, see for example, cols. 31 to 34, which is incorporated by reference herein. In some embodiments it is preferred to reduce the compound of Formula IV using hydrogen and Pd/C (palladium dispersed on carbon black) hydrogenation catalyst in some embodiments it is preferred to carry out the reduction with the compound of Formula IV dissolved in a mixed solvent comprising t-butyl-methyl ether and ethanol, preferably used in a 1:1 volumetric ratio. In some embodiments, following the reduction of the compound of Formula IV, it is preferred to collect the solution containing the compound of Formula VI(i), filter it, and treat the filtrate with aqueous acid to form the compound of Formula 2B1. In some embodiments it is preferred to collect the compound of Formula 2B1 thus formed by crystallizing it from the reaction mixture with the addition of an anti-solvent, for example, heptane. In some embodiments when the compound is precipitated it is preferred to add solid compound of the Formula 2B1 to seed the solution and aid precipitation. In some embodiments the "seed" material is prepared in accordance with the procedures described in the '342 patent. In some embodiments the "seed" material is prepared in a process carried out in accordance with the present invention either without seeding or with seeding using material prepared in an earlier process batch.

In some embodiments it is preferred to select the acid reacted with the compound of Formula VI(i) from mineral acids, for example, but not limited to $H_2SO_4$, $H_3PO_4$, HBr, and HCl, and organic acids, for example, but not limited to, maleic acid, fumaric acid, malic acid, sulfonic acids, oxalic acid, and tartaric acids and derivatives thereof. In some embodiments, when hydrochloric acid is selected, it is used as a 37N (concentrated) aqueous solution. In some embodiments, when the acid is selected from p-tolysulfonic acid, oxalic acid, and tartaric acid, it is preferred to treat the reaction mixture directly with the solid acid. It will be appreciated that the manner of precipitating the salt form of the 3-amino-2-hydroxy-benzylamide (compound of Formula 2B1) is not critical, and other methods can be employed to precipitate the salt, and other acids can be employed to precipitate their respective salts, and still be within the scope of the present invention.

Conveniently, formation of the compound of Formula 2B1 can be carried out at ambient temperature, although it will be appreciated that other temperature regimes can be employed and remain within the scope of the present invention.

Accordingly, when reacted with an acid, for example, hydrochloric acid, the compound of Formula IV(i) can be used to provide the amino-hydroxybenzamide salt compound of Formula 2B1. In some embodiments it is preferred to produce the compound of Formula 2B1 from the compound of Formula IV(i) by treating a methyl-t-butyl ether/ethanol solution of the compound of Formula IV(i) with concentrated HCl. In some embodiments it is preferred to precipitate the salt product from an isopropanol/methyl-t-butyl ether solution by adding heptane antisolvent. It will be appreciated that other acid salts, produced using the same procedure can also be employed in the reaction of Scheme III. Suitable salts include, but are not limited to, oxalate, p-tolysulfonate, monobasic tartarate, and tartarate.

There follows non-limiting examples illustrative of the present invention but not limiting the present invention.

EXAMPLES

Unless otherwise specified, all reagents are articles of commerce, food grade or pharmaceutical grade, and used as received.

Example Ia

In Situ Preparation of Dimethyl Squarate (2A2) and Reaction with Compound (2B) to Form Compound (2Ca)

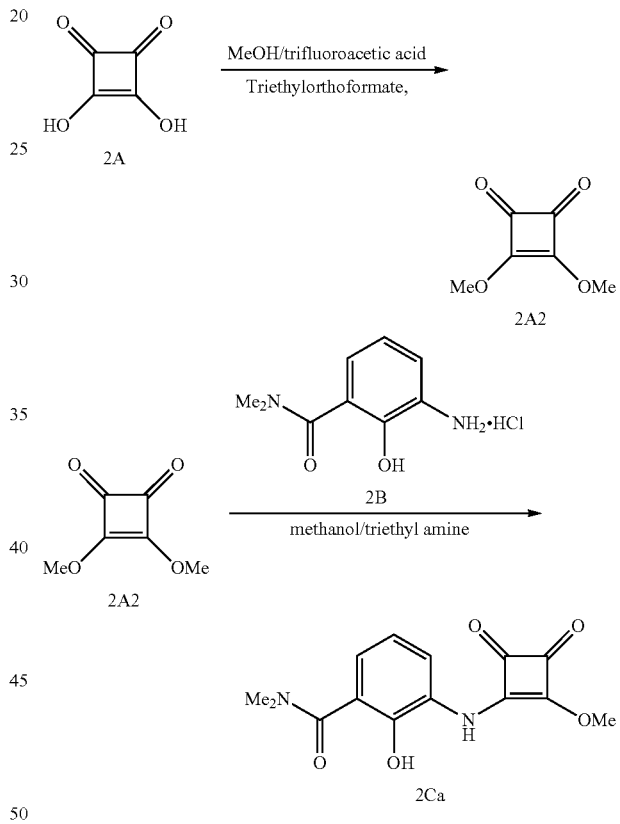

Into a 50 gallon glass reactor equipped with a thermocouple, $N_2$ inlet and feed tank was charged 9.5 kg of the compound of Formula 2A. The reactor was then charged with 65 liters dry methanol (Karl Fischer titration "KF" indicates water present at <0.1%) followed by 20 liters trimethylorthoformate and 0.2 kg trifluoroacetic acid. The reaction mixture was heated to reflux and maintained for about one hour. The reaction mixture was concentrated at one atmosphere until the internal temperature exceeded 70° C. The reaction mixture was maintained at reflux for about four hours then the temperature was adjusted to a temperature between 40° C. and 50° C. The reactor was charged with 26 liters dry methanol and the reaction mixture temperature was adjusted to about 20° C. to 30° C. The reactor was charged with 78 liters of dry methanol and the reaction mixture temperature was adjusted to a temperature between −5° C. and 5° C. The reactor was charged with 13.0 kg of the compound of Formula 2B. Triethylamine (TEA), 11.1 kg, was charged into the reactor over 4 hours while maintaining the batch at a temperature between −5 and 5° C. About one and a half hours after the start of the TEA charge, the reaction mixture was seeded with 130 grams of the compound 2C. After the addition of TEA was completed the reaction mixture was agitated for about 30 minutes maintaining the batch temperature between −5 and 5° C. Acetic acid, 12 liters was charged into the reactor while maintaining the batch at a temperature between −5 and 5° C. The reaction mixture was heated to a temperature between 60 and 70° C. and maintained in this temperature range for about 1 hour. After about 1 hour the temperature was adjusted to a temperature in the range of 25° C. to 35° C. and maintained at that temperature range for about 1 hour, then the temperature was readjusted to a temperature in the range of [−5° C.] to [+5° C.] over about 1 hour. The reaction mixture was filtered and the filter cake washed with 65 liters methanol. The solids collected were dried in a vacuum oven for about 24 hours with the oven temperature maintained at 60° C. to 70° C. Yield was 14.5 kg, about 81% based on the amount of the compound of Formula 2C employed.

$^1$HNMR(CD$_3$CN)

8.07 (1H, s); 7.56 (1H, d) 7.28 (1H, d); 6.99 (1H, t); 4.35 (3H, s); 3.10 (6H, s)

Example Ib

Preparation of the Compound of Formula (2Ca) from Commercial Dimethyl Squarate (2A2)

Charge 6.3 grams of the compound of Formula 2A1 (Aldrich, used as received) and 5.0 grams of the compound of Formula I to 250 ml round bottom flask equipped with a thermocouple, N$_2$ inlet and addition funnel. Charge 41 ml dry methanol (KF<0.1%). Adjust the batch to temperature between −5 and 5° C. Over about 5 hours, charge 4.9 ml (0.98×) triethylamine (TEA) to the batch while maintaining the batch at a temperature between −5 and 5° C. After the addition of TEA is complete, agitate the batch for about one hour at a temperature between [−5° C.] and [+5° C.]. Charge 2.8 ml acetic acid while maintaining the batch at a temperature between [−5° C.] and [+5° C.]. Adjust the batch volume to 63 ml by adding dry methanol. Heat the batch to reflux and maintain for about 15 minutes. Adjust the temperature to about [−5° C.] and [+5° C.] over about 1 hour. Filter the batch and wash the filter cake with 25 ml methanol. Dry the batch in a vacuum oven for at least 24 hours at 60 to 70° C. Yield 7.5 g, 88%.

Example Ic

Preparation of the Compound of Formula (2Ca) from Commercial Diethyl Squarate (2A3)

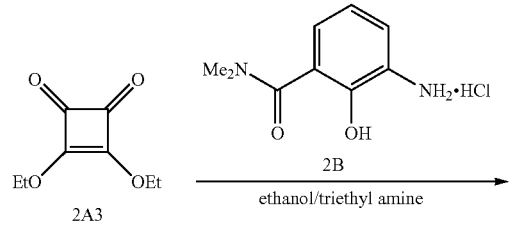

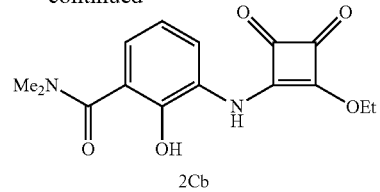

Charged 44.0 kg of the compound of Formula I, 225 kg dry ethanol and 41.8 kg of the compound of formula II to a 300 gallon glass lined reactor equipped with a thermocouple. N$_2$ inlet and feed bottle. Adjusted the batch to temperature between 0 and 10° C. Over about 1 hour, charged 17.1 kg triethylamine (TEA) to the batch while maintaining the batch at a temperature between 0° C. and 10° C. After the addition of TEA was complete, agitated the batch for about three hours at a temperature between 0° C. and 10° C. Over about 3 hours, charged additional 8.2 kg triethylamine (TEA) to the batch while maintaining the batch at a temperature between 0° C. and 10° C. After the addition of TEA was complete, agitated the batch for about three hours at a temperature between 0° C. and 10° C. Charged 19 liters acetic acid while maintaining the batch at a temperature between 0° C. and 10° C. Adjusted the batch volume to 440 liters by adding dry ethanol. Heated the batch to reflux and maintain for about 15 minutes. Adjusted the temperature to about 0° C. and 10° C. over about 2 hours. Filtered the batch and washed the filter cake with 220 liters 50% v/v ethanol in water. Dried the batch in a vacuum oven for at least 12 hours at 50 to 60° C. Yield 52 kg, 88%.

$^1$HNMR (CD$_3$CN)

7.61 (1H, d); 7.28 (1H, d); 6.96 (1H, t); 4.69 (2H, q); 3.10 (6H, s), 1.44 (3H, t).

Example IIa

Preparation of 2-Hydroxy-N,N-dimethyl-3-[[2-[[1(R)-(5-methyl-2-furanyl)propyl]amino]-3,4-dioxo-1-cyclobuten-1-yl]amino]benzamide Monohydrate (Form 4)

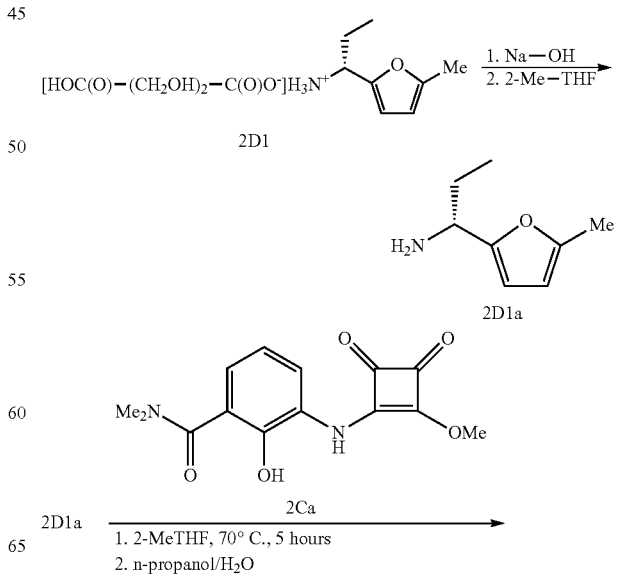

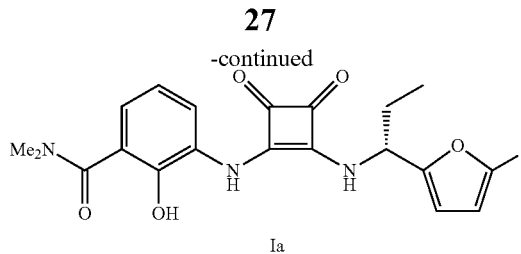

Ia

To a suspension of 10.1 g (2D1) (1.06 eq.) in 30 ml of water and 40 ml of 2-methyltetrahydrofuran was added 6.5 ml 32% of sodium hydroxide solution. The resulting aqueous layer was tested by pH paper. Additional small amount of caustic solution was added if pH was lower than 13. The organic was separated and the aqueous was extracted with 20 ml of 2-methyltetrahydrofuran. The combined organic layers was mixed with 10.0 g (1.0 eq.) of (2C) and the suspension was heated at 70° C. for 5 hours until the remaining starting material was below 1.0%. N-Propanol (50 ml) was added. The volume of the reaction mixture was reduced by distillation under partial vacuum to 40 ml (4×), followed by addition of 50 ml of n-propanol. The volume of the solution was reduced again under partial vacuum to 60 ml. The mixture was diluted to 90 ml with n-propanol and 0.3 ml of acetic acid was charged. The solution was then filtered. The filtrate was then diluted to 140 ml with n-propanol and the solution was heated to 70° C. Water (125 ml) was added while the batch temperature was maintained above 70° C. The solution was cooled to 62° C. and 200 mg (0.02×) seeds of the compound of Formula I (Form 4, previously prepared) were added. The mixture was stirred at 62° C. for 2 hours before it was cooled to 20° C. over about 5 hours. The suspension was then warmed up to 55° C. over 30 minutes before slowly cooling to 20° C. over 4 hours. The heating and cooling operation was repeated several times to grow crystals of the desired particle size. The suspension was finally cooled to 20° C. before filtration. The wet cake was washed with 80 ml solvent mixture of n-propanol and water (1:1). The cake was dried at 50° C. for 12 hours or until KF analysis showed the water content was below 4.7%, to give 11.5 g (85%) white needles, m.p. 83° C. XRD analysis showed the crystal form of the solids was form 4 monohydrate. $^1$H NMR (DMSO-D6) δ, 0.91 (t, 3H, 1.84 (m, 1H), 1.94 (m, 1H), 2.25 (s, 3H), 2.92 (S, 6H), 5.13 (m, 1H), 6.01 (d, 1H, J=3.1), 6.25 (d, 1H, J=3.1), 6.85 (m, 2H), 7.78 (d, 1H, J=7.3), 8.65 (d, 1H, J=8.9), 9.29 (br, 1H), 9.99 (br, 1H). $^{13}$C NMR (DMSO-D6): 10.26, 13.32, 27.18, 52.78, 106.42, 107.52, 119.77, 120.76, 122.18, 124.42, 128.64, 143.25, 151.31, 152.06, 163.41, 168.27, 168.52, 180.17, 183.95, 184.71. Anal. calcd. for $C_{12}H_{25}N_3O_6$ (monohydrate 415.4): C, 60.71; H, 6.07; N, 10.11. Found: C, 60.65; H, 5.93; N, 9.91.

Example IIb

Preparation of 2-Hydroxy-N,N-dimethyl-3-[[2-[[1(R)-(5-methyl-2-furanyl)propyl]amino]-3,4-dioxo-1-cyclobuten-1-yl]amino]benzamide Monohydrate (Form 4)

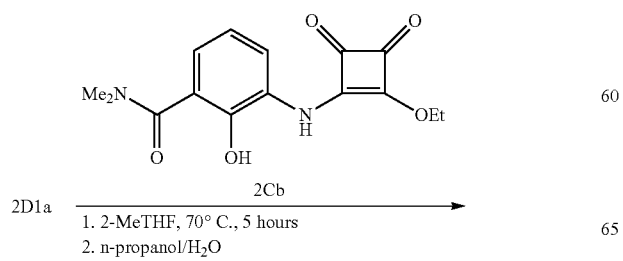

2D1a →
1. 2-MeTHF, 70° C., 5 hours
2. n-propanol/H₂O

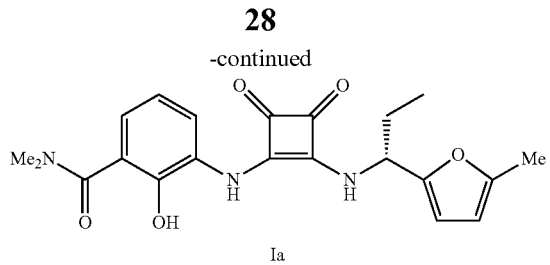

Ia

Following the same procedure used in Example IIa, 40.2 kg of 2D1 was treated with the base to make 2D1a, which was subsequently reacted with 39.8 kg of 2Cb (made previously from diethylsquarate), to give 43.8 kg (81%) of the title compound.

Example III

Preparation of 2-Hydroxy-N,N-dimethyl-3-amino-benzamide Salts (2B1)

There follows four examples of the preparation of the hydrochloride, oxalate, p-tolysulfonate, and tartarate salts of 3-amino-2-hydroxy-benzamide in accordance with Scheme V, below.

SCHEME V

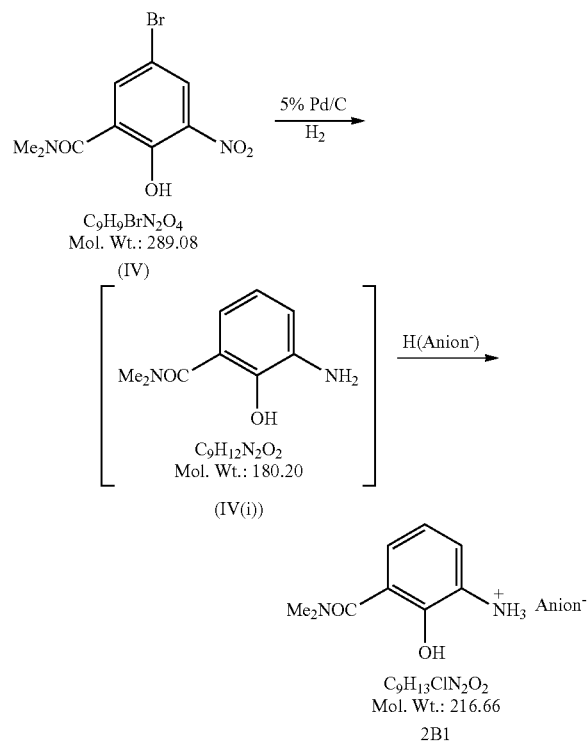

2B Anion⁻ = Cl⁻
2B2 Anion⁻ = Oxalate⁻
2B3 Anion⁻ = p-Tosylate⁻
2B4 Anion⁻ = Tartarate⁻

Example III a

Preparation of Compound 2B (HCl salt of 3-amino-2-hydroxy-benzamide (compound (IV(i)))

To a suspension of 10 g (34.6 mmol) of (IV) in a mixture of 21 ml of methyl t-butylether and 49 ml of ethanol was added 13.7 ml of KOEt (24%) in ethanol, followed by addition of 0.8 g of 5% Pd/C (50% wet). The mixture was then agitated under 120-150 psi hydrogen pressure for about 6 hours. Upon completion of the reaction, the batch was filtered through a Celite pad and the cake was washed with 80 ml of solvent mixture of methyl t-butylether and ethanol (1:1). The filtrate was treated with 3.7 ml of concentrated HCl solution. The batch was then concentrated under reduced pressure to about 50 ml. Isopropanol (100 ml) was added and the resulting solution was concentrated under vacuum to about 40 ml. Methyl t-butylether (50 ml) was added, followed by a slow addition of 110 ml of heptane. Finally, the mixture was cooled to 0° C. The solids were collected by filtration and the cake was washed with 20 ml solvent mixture of 1:1 methyl t-butylether/EtOH. The cake was dried at 60° C. for 10 hours in a vacuum oven, to give 7.24 g (96%) off-white solids of the compound of Formula 2B. $^1$H NMR (DMSO-D6): 7.50 (d, 1H), 6.96 (dd, 1H), 7.17 (d, 1H), 2.9 (br, 6H), 10.2 (br, 4H), $^{13}$C NMR (DMSO-D6): 147.7, 121.4, 125.9, 120.6, 128.5, 127.1, 167.8.

Example IIIb

Preparation of 3-amino-2-hydroxy-benzamide Oxalate Salt (2B2),

Following the procedure described for preparing the HCl salt (2B) in Preparative Example 1, 10 g (34.6 mmol) of compound (IV) was hydrogenated under the same condition and the filtered solution was treated with 3.3 g of oxalic acid. Following the same procedure as above resulted in 8.5 g (90%) off-white solids, $^1$H NMR (DMSO-D6): 6.45 (m, 2H), 6.17 (dd, 1H), 2.70 (s, 6H). 5.5 (very broad, 4H).

Example IIIc

Preparation of 3-amino-2-hydroxy-benzamide p-Tolysulfonate Salt (2B3)

Following the procedure described for preparing the HCl salt (2B) in Preparative Example 1, the compound of Formula 2B3 was prepared by placing 10 g of compound (IV) was hydrogenated under the same condition and the filtrate was treated with 7.9 g (41.1 mmol) p-toluenesulfonic acid monohydrate. The resulting mixture was concentrated as above and the mixture after heptane addition was stirred over night at room temperature, to give 11.4 g (94%) off-white solids. $^1$H NMR (DMSO-D6): 7.49 (d, 2H), 7.29 (d, 1H), 7.15 (m, 3H), 6.93 (dd, 1H), 2.90 (s, 6H), 2.31 (s, 3H),

Example IIId

Preparation of 3-amino-2-hydroxy-benzamide tartarate Salt

Following the procedure described for preparing the HCl salt (2B) in Preparative Example 1, the compound of Formula 2B4 was prepared by placing 10 g of compound (IV) was hydrogenated under the same condition and the filtrate was treated with 5.47 g (36.5 mmol) of tartaric acid. Following the same procedure as described in 527123-PS preparation resulted in 9.1 g (80%) of off-white solids. $^1$H NMR (DMSO-D6): 8.5 (br, 3H), 6.6 (dd, 2H), 6.38 (d, 1H), 4.26 (s, 2H), 3.6 (b, 2H), 2.96 (s, 6H).

Example IV

Preparation of Amino-Furan Salt Intermediates (2Da)

There follows three examples of preparing various salt compounds of the Formula 2Da

Example IVa

Preparation of tartarate salt of α-(R)-Ethyl-5-methyl-2-furanmethanamine D-tartrate (2Da1)

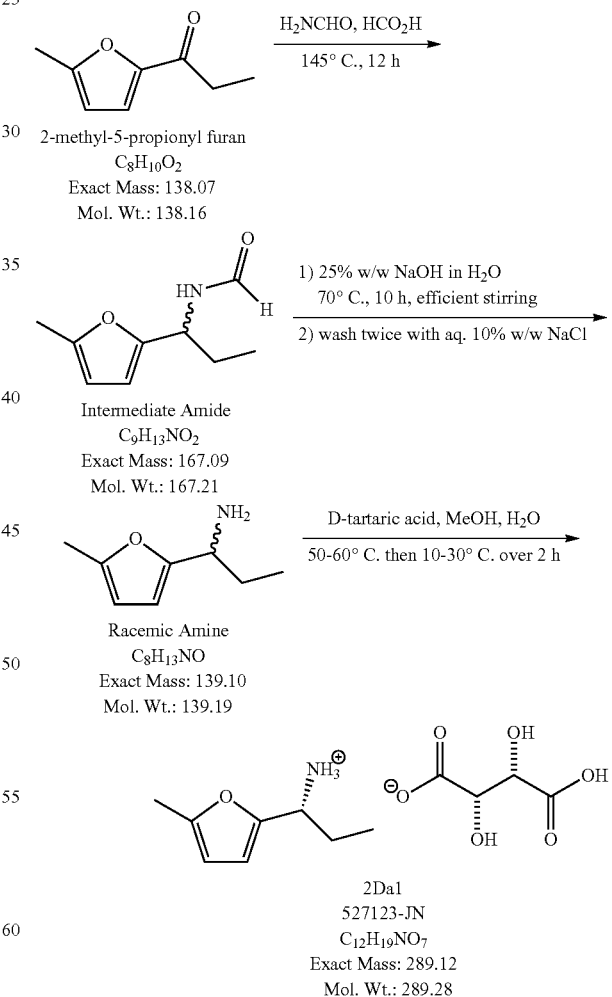

2-methyl-5-propionyl furan
C$_8$H$_{10}$O$_2$
Exact Mass: 138.07
Mol. Wt.: 138.16

Intermediate Amide
C$_9$H$_{13}$NO$_2$
Exact Mass: 167.09
Mol. Wt.: 167.21

Racemic Amine
C$_8$H$_{13}$NO
Exact Mass: 139.10
Mol. Wt.: 139.19

2Da1
527123-JN
C$_{12}$H$_{19}$NO$_7$
Exact Mass: 289.12
Mol. Wt.: 289.28

To a stirred solution of 100 g 2-methyl-5-propionylfuran (1.0 equiv., 0.724 mol) and 115 mL formamide (2.90 mol, 4.0 equiv.) at 25° C. was added 30.0 mL formic acid (0.796 mol, 1.1 equiv.). A small exotherm was observed. The resulting solution was heated to 140-150° C. over 1 hour, held at this temperature for 12 hours, and then cooled to 20-30° C. over 1 hour. To the stirred solution of crude intermediate amide product was added 641 mL 25% w/w aq. NaOH (5.07 mol NaOH, 7.0 equiv.). An exotherm was observed. The heterogeneous solution was vigorously agitated to achieve a homogeneous mixture. The solution was heated to 65-70° C. over 30 min., held at this temperature for 10 hours, then cooled to 20-30° C. over 1 hour. The phases were allowed to separate, drained the aqueous layer, then washed the organic layer of crude racemic amine twice with 10% aq. NaCl (100 mL). The crude racemic amine was taken up in 350 mL methanol and 28 ml water. The solution was heated to 50-60° C. and to it was added 73.5 g D-tartaric acid (0.502 mol, 1.0 equiv.) as a solution in 210 mL, methanol and 14 mL water over 30 minutes. The reaction was held at 60° C. for 15 min, then cooled to 15-35° C. over 2 hours. The suspension was then filtered under vacuum and washed twice with 70 mL methanol. The wet cake was dried in a vacuum oven at 50-60° C. for at least 8 hours to afford 60.1 g (28.7% yield, 99% se) of a white crystalline solid; mp=191-194° C.; $^1$H NMR (DMSO-D6): δ 0.81 (t, 3H, J=7.4 Hz), 1.79-1.95 (m, 2H), 2.26 (s, 3H), 3.99 (s, 2H), 4.18 (dd, 1H, J=8.9, 5.7 Hz), 6.07 (dd, 1H, J=3.1, 1.1 Hz), 6.38 (d, 1H, J=3.1 Hz), and 8.16 (brs, 6H). $^{13}$C NMR (DMSO-D6): 10.31, 13.63, 25.46, 49.40, 72.31, 107.03, 109.98, 149.46, 152.01, 175.01 ppm.

Example IVa

Alternative Preparation of tartarate salt of α-(R)-Ethyl-5-methyl-2-furanmethanamine D-tartrate (2Da1)

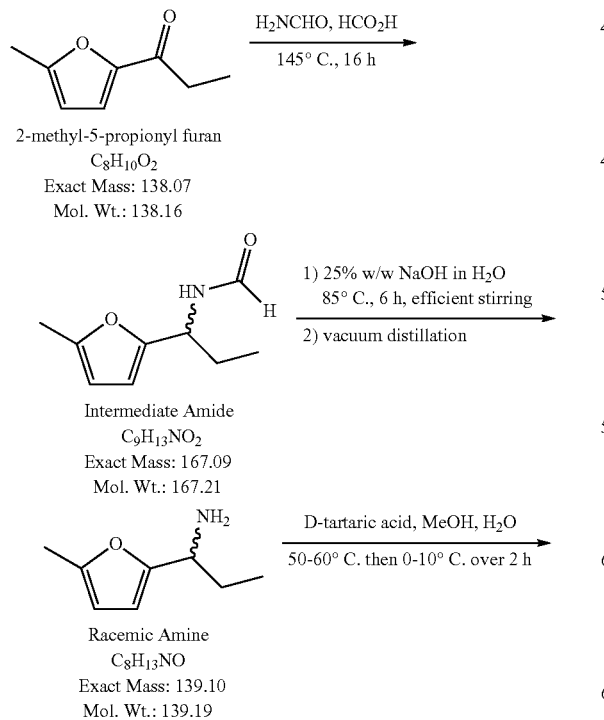

2-methyl-5-propionyl furan
C$_8$H$_{10}$O$_2$
Exact Mass: 138.07
Mol. Wt.: 138.16

Intermediate Amide
C$_9$H$_{13}$NO$_2$
Exact Mass: 167.09
Mol. Wt.: 167.21

Racemic Amine
C$_8$H$_{13}$NO
Exact Mass: 139.10
Mol. Wt.: 139.19

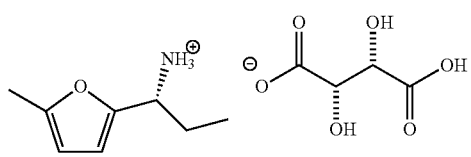

2Da1
527123-JN
C$_{12}$H$_{19}$NO$_7$
Exact Mass: 289.12
Mol. Wt.: 289.28

To a stirred solution of 60 g 2-methyl-5-propionylfuran (1.0 equiv., 0.434 mol) and 69 mL formamide (1.74 mot, 4.0 equiv.) at 25° C. was added 16.4 mL formic acid (0.434 mol, 1.0 equiv.). The resulting solution was heated to 140-150° C. over 1 hour, held at this temperature for 16 hours, and then cooled to 20-30° C. over 1 hour. To the stirred solution of crude intermediate amide product was added 377 mL 25% w/w aq. NaOH (2.89 mol NaOH, 7.0 equiv.). The heterogeneous solution was vigorously agitated to achieve a homogeneous mixture. The solution was heated to 80-90° C. over 30 min., held at this temperature for 6 hours, then cooled to 20-30° C. over 1 hour. The phases were allowed to separate, and the aqueous layer was drained. The crude racemic amine was distilled under vacuum (20-25 mmHg) to afford 50.1 g (82% yield) of a pale yellow oil; bp=60-65° C. (40-45 mmHg): $^1$H NMR (DMSO-D6) δ 0.84 (3H, t, J=7.4 Hz), 1.49-1.58 (1H, m), 1.81-1.71 (1H, m), 1.61 (2H, brs), 2.21 (3H, s), 3.63 (1H, t, J=6.54 Hz), 5.93 (1H, dd, J=2.98, 1.00 Hz), 6.00 (1H, d, J=1.0 Hz); $^{13}$C NMR (DMSO-D6): 10.6, 13.6, 29.7, 51.1, 105.2, 106.1, 149.8, 158.5 ppm. To a solution of the racemic amine in 250 mL methanol was added 50.5 g D-tartaric acid (336.5 mmole) as a solution in 150 mL methanol over 30 minutes. The solution was heated to 40-50° C. and held at this temperature for 20 minutes. The reaction was slowly cooled to 0-10° C. over 2 hours. The suspension was then filtered under vacuum and washed with methanol (100 mL). The wet cake was dried in a vacuum oven at 50-60° C. for at least 8 hours to afford 44.1 g (42.3% yield from racemic amine, 94% ee) of a white crystalline solid; characterized as above.

Example IVa

Preparation Using a Coacid in Resolution of tartarate salt of α-(R)-Ethyl-5-methyl-2-furanmethanamine D-tartrate (2Da1)

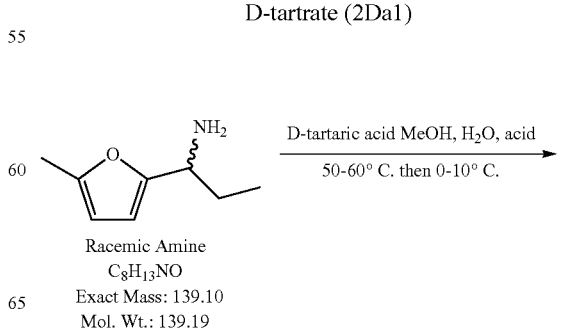

Racemic Amine
C$_8$H$_{13}$NO
Exact Mass: 139.10
Mol. Wt.: 139.19

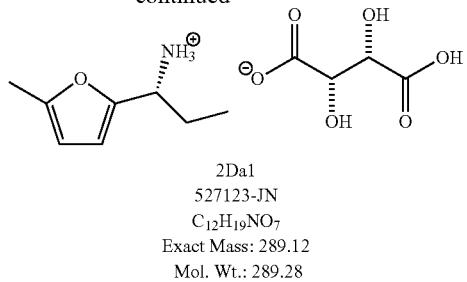

2Da1
527123-JN
C₁₂H₁₉NO₇
Exact Mass: 289.12
Mol. Wt.: 289.28

To a solution of racemic amine (5.0 g, 35.9 mmole, prepared as described above) in methanol (25 mL) and water (1.8 mL) was added an acid (0.5 equiv., 18.0 mmole, see table below). The solution was warmed to 60° C. A solution of D-tartaric acid (3.23 g, 21.6 mmole, 0.6 equiv.) in methanol (15 mL) was added dropwise over 10 min. The reaction was held at 60° C. for 20 min., cooled to 25° C. over 90 minutes, and seeded with a small amount of product. After product precipitated the suspension was cooled to 0-10° C. over 30 minutes, held 30 minutes, then filtered under vacuum and washed with methanol (10 mL). The wet cake was dried in a vacuum oven for 12 hours to afford a white crystalline solid (see table below for yield).

| Acid | Yield (%) | Ee (%) |
| --- | --- | --- |
| none | 19.3 | 96.5 |
| acetic acid | 34.2 | 98.9 |
| formic acid | 39.1 | 97.3 |
| malonic acid | 44.7 | 98.5 |
| hydrochloric acid | 43.2 | 99.0 |
| chloroacetic acid | 44.9 | 98.4 |
| trifluoroacetic acid | 44.8 | 99.4 |

Example V

Preparation of 2-hydroxy-N,N-dimethyl-3-[[2-[[1(R)-[5-methyl-4-(1-methylethyl)-2-furanyl]propyl]-amino]-3,4-dioxo-1-cyclo-buten-1-YL]amino]-benzamide (the compound of Formula II)

There follows two examples of the preparation of a compound of Formula II according to the following scheme:

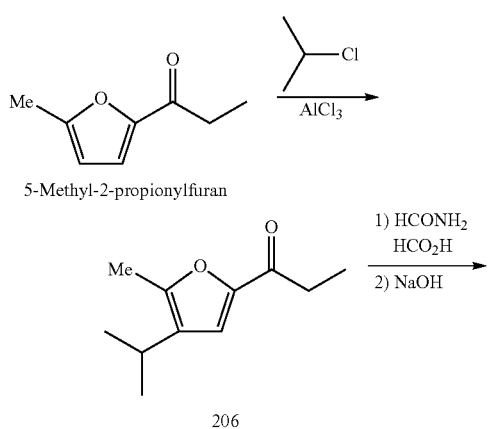

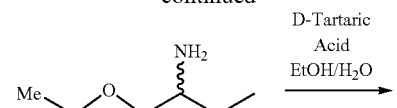

207

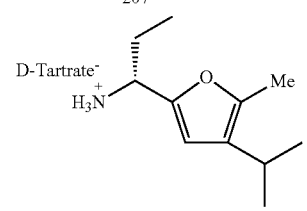

208

+

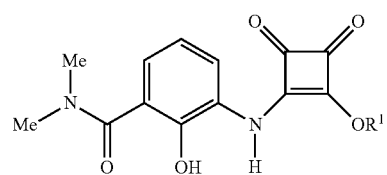

209A: R¹ = methyl
209B: R¹ = ethyl

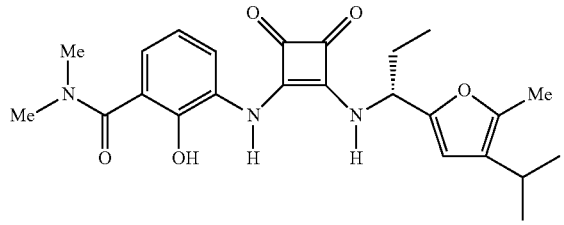

II

Example Va utilizes a methyl-THF workup to isolate the final product, example Vb utilizes an isopropyl alcohol workup to isolate the final product.

Example Va

Step 1: 1-(4-Isopropyl-5-methyl-2-furyl)propan-1-one (206)

Under nitrogen, 2-methyl-5-propionylfurane (100 g, 0.72 moles) was added dropwise at 0-30° C. to aluminium chloride (131 g, 0.96 moles). The resulting suspension was stirred for further 30 minutes at room temperature and then cooled to 0-5° C. Within one hour isopropyl chloride (76 g, 0.96 moles) was added dropwise at 0-10° C. and the mixture stirred until complete conversion was achieved (HPLC). The mixture was hydrolyzed on 2 L of water/ice. The pH was adjusted to 1 by addition of sodium hydroxide solution (60 mL) and the product was extracted into 500 mL TBME. The aqueous layer was separated and reextracted with 200 mL TBME. The combined organic layers were washed with 500 mL brine and evaporated to minimum volume. Yield: 132.5 g (102%) of a yellow-brown liquid.

Assay (HPLC: YMC Pack Pro C18 150×4.6 mm, 5 μm; 220 nm; ACN/0.05% TFA: water/0.05% TFA 20:80 to 95:5 within 23 min): 60% pure by area, RT 17.2 min.

Step 2:
[1-(4-Isopropyl-5-methyl-2-furyl)propyl]amine (207)

Under nitrogen, a mixture of crude 1-(4-Isopropyl-5-methyl-2-furyl)propan-1-one (100 g), formamide (100 g, 2.22 moles) and formic acid (28.7 g, 0.61 moles) was heated to 140° C. for about two days until complete conversion to intermediate N-(1-(4-isopropyl-5-methylfuran-2-yl)propyl) formamide was achieved. The mixture was cooled to 20-25° C. and diluted with 400 mL methanol and 400 mL diisopropylether. Aqueous sodium hydroxide (1.2 kg, 25% in water) was added and the mixture was heated to reflux (55-60° C.) for about one day until complete conversion to [1-(4-Isopropyl-5-methyl-2-furyl)propyl]amine was achieved. The mixture was cooled down to 20-25° C. and the phases were separated. The organic layer was washed with 400 mL brine (5% in water). The combined aqueous layers were reextracted with 200 mL diisopropylether. The combined organic layers were evaporated to minimum volume. Yield: 94.6 g (45% abs (absolute), from 2-methyl-5-propionylfurane) of a yellow-brown liquid.

Assay (HPLC: YMC Pack Pro C18 150×4.6 mm, 5 µm; 220 nm; ACN/0.05% TFA: water/0.05% TFA 20:80 to 95:5 within 23 min): 48.5% pure vs. standard, RT 9.2 min.

Step 3: (R)-1-(4-Isopropyl-5-methylfuran-2-yl)propan-1-amine (2S,3S)-2,3-dihydroxysuccinate (208)

Under nitrogen, crude [1-(4-isopropyl-5-methyl-2-furyl) propyl]amine (51 g, 135 mmol active) was dissolved in 204 mL dry ethanol at 60° C. 20% of a solution of D-(−)-tartaric acid (20.3 g, 135 mmol) in a mixture of 102 mL ethanol/water (15:1) was added at 55° C. The solution was seeded. The residual solution of tartaric acid was added within 10 minutes. The suspension was cooled to 20° C. and stirred at room temperature over night. The salt was filtered off and washed with dry ethanol until a colorless mother liquor was obtained. The product was dried in vacuum at 50° C. to constant weight. Yield: 16.9 g (38% abs.) of white crystals.

Assay (HPLC: YMC Pack Pro C18 150×4.6 mm, 5 µm; 220 nm; ACN:0.01M $KH_2PO_4$ pH=2.5 ($H_3PO_4$) 15:85 to 80:20 within 25 min): 95.8% by area, RT 8.8 min.

Optical Purity (HPLC: Chiralcel OD-R 250×4.6 mm; 226 nm; ACN:0.5M $NaClO_4$ 40:60): dr 98:2, RT 12.6 min (R), 16.3 min (S). Wherein "dr" represents diastereomeric ratio.

Step 4: 2-Hydroxy-3-[(2-{[(1R)-1-(4-isopropyl-5-methyl-2-furyl)propyl]amino}-3,4-dioxocyclobut-1-en-1-yl)amino]-N,N-dimethylbenzamide (Compound II)

Under nitrogen, (R)-1-(4-Isopropyl-5-methylfuran-2-yl) propan-1-amine (2S,3S)-2,3-dihydroxy-succinate (208)(2.0 g, 6 mmol) was suspended in 6 ml water and 8 mL 2-methyl tetrahydrofurane (MeTHF) at 20-25° C. 1.3 mL aqueous sodium hydroxide (30%) were added and the organic layer was separated after 5 minutes. The aqueous layer was extracted with 4 mL MeTHF. The combined organic layers were added to (209B) (1.74 g, 5.7 mmol) and 4 mL MeTHF were added. The mixture was heated to 65° C. for 4.5 hours and was then cooled to 20-25° C. After 16 hours at 20-25° C. the product crystallized and was isolated by filtration. The product was washed with MeTHF and dried in vacuum at 50° C. to constant weight. Yield: 1.25 g (47%) as off-white solid. Assay (NMR): 95% pure.

If one were to use compound (209A) in place of compound (209B) in Step 4 of Example IV, one would also obtain compound (II) using this same procedure.

Example Vb

Step 1 1-(4-Isopropyl-5-methyl-2-furyl)propan-1-one (206)

Under nitrogen, 2-methyl-5-propionylfurane (120 g, 0.87 moles) was added dropwise at 0-35° C. to aluminium chloride (158 g, 1.18 moles) in dichloromethane (60 mL). The resulting solution was stirred for further 30 minutes at room temperature and then cooled to 0-5° C. Within one hour isopropyl chloride (96 g, 1.21 moles) was added dropwise at 0-10° C. and the mixture was stirred at 0-5° C. until complete conversion was achieved. The mixture was hydrolyzed on 2 L of water/ice and TBME (480 mL) was added. The pH was adjusted to 1 by addition of sodium hydroxide solution 30% (50 mL) and the phases were split. The aqueous layer was reextracted into 240 mL TBME. The combined organic layers were washed with 300 mL brine twice and evaporated to minimum volume. Yield: 168 g (107%) of a yellow-brown liquid.

Assay (HPLC: YMC J'sphere ODS-H80 150×4.6 mm, 4 µm; 220 nm; ACN/0.01M $KH_2PO_4$ pH 2.5 ($H_3PO_4$) 55:45 to 80:20 within 15 min): 55% pure by area, RT 6.6 min.

Step 2
[1-(4-Isopropyl-5-methyl-2-furyl)propyl]amine (207)

Under nitrogen, a mixture of crude 1-(4-Isopropyl-5-methyl-2-furyl)propan-1-one (206) (164 g), formamide (158 g, 3.5 moles) and formic acid (46 g, 0.98 moles) was heated to 140° C. for about two days until complete conversion to intermediate N-(1-(4-isopropyl-5-methylfuran-2® yl)propyl) formamide was achieved. The mixture was cooled to 20-25° C. and diluted with 624 mL, methanol and 624 mL, diisopropylether. Aqueous sodium hydroxide (1.9 kg, 25% in water) was added and the mixture was heated to reflux (55-60° C.) for about one day until complete conversion to [1-(4-Isopropyl-5-methyl-2-furyl)propyl]amine (207) was achieved. The mixture was cooled down to 20-25° C. and the phases were separated. The organic layer was washed with 624 mL brine (5% in water). The combined aqueous layers were reextracted with 312 mL diisopropylether. The combined organic layers were evaporated to minimum volume. Yield: 149 g (37% abs. from 2-methyl-5-propionylfurane) of a brown liquid.

Assay (HPLC: YMC Pack Pro C18 150×4.6 mm, 5 µm; 220 nm; ACN/0.01M $KH_2PO_4$ pH 2.5 ($H_3PO_4$) 15:85 to 80:20 within 25 min): 56% pure by area, RT 8.7 min.

Step 3 (R)-1-(4-Isopropyl-5-methylfuran-2-yl)propan-1-amine (2S,3S)-2,3-dihydroxysuccinate (208)

Under nitrogen, crude [1-(4-isopropyl-5-methyl-2-furyl) propyl]amine (207) (151 g, 0.35 mol active) was dissolved in 440 mL, ethanol at 40° C. 55% of a solution of D-(−)-tartaric acid (60.6 g, 0.40 mol) in 337 mL ethanol was added at 40° C. The solution was seeded and the residual tartaric acid solution was added slowly. The suspension was cooled to 20° C. and stirred at room temperature for additional two hours. The salt was filtered off and washed with ethanol until a colorless product was obtained. The product was dried in vacuum at 40 to 50° C. to constant weight. Yield: 50 g (42% abs.) of white crystals.

Assay (HPLC: YMC Pack Pro C18 150×4.6 mm, 5 μm; 220 nm; ACN:0.01M KH$_2$PO$_4$ pH=2.5 (H$_3$PO$_4$) 15:85 to 80:20 within 25 min): 96.5% by area, RT 8.6 min. Optical Purity (HPLC: Chiralcel OD-R 250×4.6 mm; 226 nm; ACN:0.5M NaClO$_4$ 40:60): dr 98:2 R:S, RT 11.4 min (R), 14.8 min (S)

Step 4 2-Hydroxy-3-[(2-{[(1R)-1-(4-isopropyl-5-methyl-2-furyl)propyl]amino}-3,4-dioxocyclobut-1-en-1-yl)amino]-N,N-dimethylbenzamide (Compound II)

Under nitrogen, (R)-1-(4-Isopropyl-5-methylfuran-2-yl)propan-1-amine (2S,3S)-2,3-dihydroxy-succinate (208) (60 g, 0.18 mmol) was suspended if 180 mL water and 240 mL 2-methyl tetrahydrofurane (MeTHF) at 20-25° C. 51 g aqueous sodium hydroxide (30%) was added dropwise and the organic layer was separated. The aqueous layer was reextracted with 120 ml. MeTHF. The combined organic layers were added to (209B) (51.8 g, 0.17 mol active) and the mixture was heated to 65° C. for 4.5 hours. After complete conversion was obtained the mixture was evaporated to a volume of about 175 mL. To the concentrated reaction mixture was added 2-Propanol (450 mL) and the mixture was concentrated to about 250 mL. Another 100 mL of 2-propanol were added and removed again. The mixture was filtered and washed with 180 mL hot 2-propanol. At 40° C. water (5 mL) and seeds (0.5 g) were added followed by dropwise addition of a mixture of water (25 mL) and 2-propanol (50 mL). At 40° C. further 450 mL water were added and the suspension was cooled to 20-25° C. The product was filtered off and washed 4 times with 100 mL of a mixture of water/2-propanol (1:1) each. The product was dried under vacuum at 35-40° C. to constant weight. Yield: 67.6 g as monohydrate (83% abs.).

Assay (HPLC: YMC Pack Pro C18 150×4.6 mm, 5 μm; 220 nm; ACN:0.01M KH$_2$PO$_4$ pH=2.5 (H$_3$PO$_4$) 20:80 to 70:30 within 10 min): 96.3% by area, RT 12.5 min. Optical Purity (HPLC: Astec, Cyclobond I 2000 RN, 250×4.6 mm, 5 μm; 293 nm): dr 99:1 R:S, RT 12.9 min (R), 10.9 min (S)

$^1$H-NMR (CDCl$_3$, 300 MHz): 7.65 (d, 1H, Ph), 6.75 (d, 1H, Ph), 6.65 (dd, 1H, Ph), 6.03 (s, 1H, fur), 5.1 (m, 1H, CHEt), 3.00 (s, 6H, NMe$_2$), 2.6 (sept, 1H, iPr), 2.07 (s, 3H, Me), 1.8 (m, 2H, Et), 1.02 (d, 6H, iPr), 0.85 (t, 3H, Et) ppm.

The above description of the invention is intended to be illustrative and not limiting. Various changes or modifications in the embodiments described herein may occur to those skilled in the art. These changes can be made without departing from the scope or spirit of the invention

What is claimed is:

1. A process for making the compounds of Formula A,

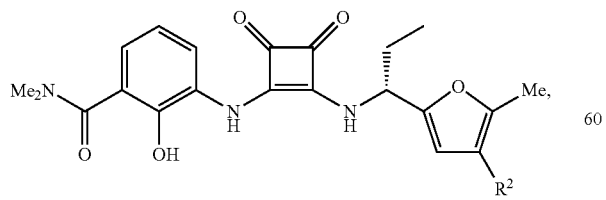

Formula A the process comprising:
(a) forming the dialkyl-squarate of Formula A1 in situ by reacting (R$^3$—O—)$_3$—CH with squaric acid,

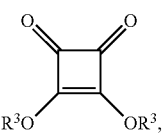

Formula A1 wherein R$^3$ is selected from linear, branched, and cyclic alkyls of up to 10 carbon atoms;
(b) reacting the amino-hydroxy-benzamide compound of Formula B

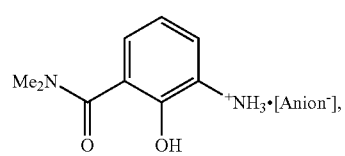

Formula B wherein [Anion$^-$] is a monovalent anionic moiety, with the dialkylsquarate from step "a" to form the compound of Formula C,

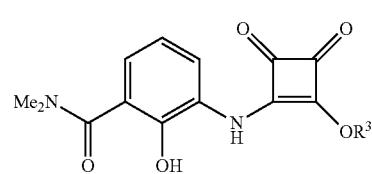

Formula C wherein R$^3$ is as defined above;
(c) reacting the compound of formula C formed in step "b" with a free base amino-furan compound of formula D1 formed in situ,

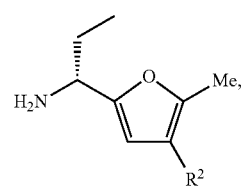

Formula D1 wherein R$^2$ is H or a substituent comprising from 1 carbon atom to about 10 carbon atoms selected from linear, branched, or cyclic alkyl moieties and substituted linear, branched and cyclic alkyl moieties, to provide the compound of formula A; and
(d) optionally precipitating the compound of Formula A by:
(i) successive cycles of concentrating the reaction mixture formed in step "c" by distillation followed by the addition of an aliquot of an alcohol;
(ii) adding an aliquot of the alcohol used in Step "d(i)" and acetic acid to the concentrate formed in step "i";
(iii) heating the solution formed in step "ii";
(iv) adding an aliquot of water and seed crystals to the hot solution from step "iii";

(v) cycling the temperature of the seeded solution prepared in step "iv" until crystals of the compound of Formula A having a desired size are formed; and (vi) optionally isolating the crystals from the mixture prepared in step "v".

2. The Process of claim 1 wherein $R^2$ is H or isopropyl, step "b" is carried out with the addition of triethylamine, and when optional step "d" is carried out, the alcohol used in step "d(i)" is isopropanol or normal propanol.

3. The process of claim 2 wherein "$R^3$—" in the dialkylsquarate formed in step "a" is $H_3C$— or $H_3C$—$(H_2)C$— and is formed by reacting squaric acid of formula Q,

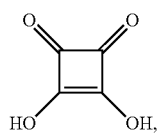

Formula Q with a trialkylorthoformate of the Formula $(R^3O)_3$—CH in an alcohol of the Formula $R^3OH$, wherein, when the dialkyl squarate is dimethyl squarate, "$R^3$—" in both the alcohol and trialkylorthoformate is [$H_3C$—], and when the dialkylsquarate is diethylsquarate, "$R^3$—" in both the alcohol and trialkylorthoformate is [$H_3C$—$(H_2)C$—].

4. The process of claim 3 wherein the reaction is carried out in the presence of trifluoroacetic acid.

5. The process of claim 4 wherein after formation of the compound of Formula C the process comprises the additional steps of: isolating the compound of Formula C by heating the reaction mixture with acetic acid; cooling the reaction mixture to precipitate the compound of Formula C; and collecting the precipitate by filtration.

6. The process of claim 5 wherein step "b", reacting the compound of Formula B with dialkyl squarate, is carried out at a temperature of from about −5° C. to about +5° C. and is carried out with the addition of triethyl amine added to the reaction mixture over a portion of the reaction period.

7. The process of claim 6 wherein "$R^3$—" is [—$CH_3$], in step "a", in situ preparation of dimethyl squarate is carried out in refluxing methanol and the reaction mixture provided by step "a" is concentrated prior to reacting it with the compound of Formula B.

8. The process of claim 6 wherein in step "b", the reaction mixture containing the compound of Formula C is seeded with a solid form of the compound of Formula C to precipitate the compound from the reaction mixture.

9. The process of claim 8 wherein the reaction mixture prepared in step "b" is worked up by heating the reaction mixture with acetic acid and then cooling the reaction mixture to precipitate solid compound of Formula C.

10. The process of claim 1 wherein optional step "d" is carried out by adding an aliquot of n-propanol, concentrating the reaction mixture by distillation, adding a second aliquot of n-propanol, concentrating the mixture a second time by distillation, adding a third aliquot of n-propanol and acetic acid, filtering the reaction mixture, adding additional n-propanol and heating the mixture, then adding water, seeding the mixture with crystals of the compound of Formula A and cooling the mixture.

11. The process of claim 10 wherein optional step "d" is carried out by cycling the temperature of the filtered n-propanol/acetic acid mixture between ambient temperature and a temperature of from about 55° C. to about 70° C. until crystals of a desired size are formed.

12. The process of claim 1 wherein step "c", forming the free base amino-furan compound of Formula D1 is carried out by reacting an aqueous base with the compound of Formula D,

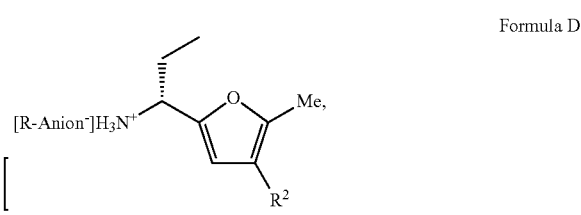

Formula D where [R-Anion⁻] is a monovalent anion and $R^2$ is hydrogen or an alkyl substituent selected from linear, branched, and cyclic alkyl moieties and substituted linear, branched, and cyclic alkyl moieties having from 1 carbon atom to about 10 carbon atoms.

13. The process of claim 12 wherein the base used to prepare the compound of Formula D1 is sodium hydroxide, [R-Anion⁻] in the compound of Formula D is an optically active monovalent anionic moiety capable of preferentially forming a salt of the R-isomer of the compound of Formula 2D,

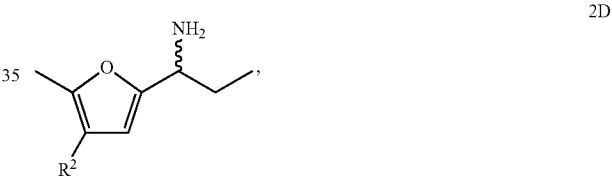

2D $R^2$ is hydrogen or isopropyl, and the reaction is carried out in a solvent comprising 2-methyl-tetrahydrofuran.

14. A process for the preparation of compound of Formula 2C,

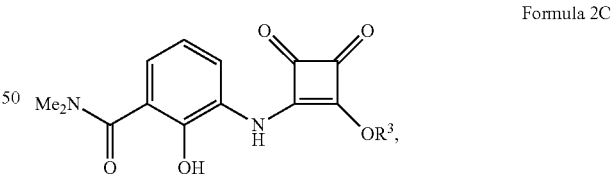

Formula 2C the process comprising:

(a) forming dialkyl-squarate of Formula A1,

Formula A1 in situ by reacting $(R^3O)_3CH$ with squaric acid, wherein [$R^3$—] is ethyl or methyl; and (b) reacting the dialkylsquarate formed in step "a" with an amino-hydroxide benzamide salt compound of Formula 2B, wherein "Anion⁻" is a monovalent anionic moiety, Formula 2B

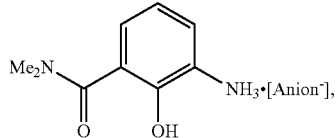

to form the compound of Formula 2C.

15. The process of claim 14 wherein the reaction step "a" is carried out in refluxing methanol in the presence of trifluoroacetic acid.

16. A process for making the salt compound of Formula 2Da

Formula 2Da

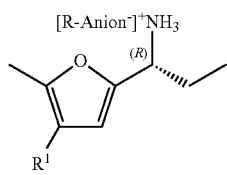

the process comprising:

(a) reductively aminating the compound of Formula (2Dd) by treatment with formamide in the presence of formic acid, Formula 2Dd

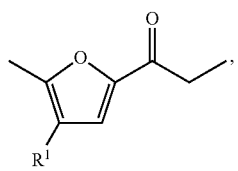

wherein R¹ is hydrogen or a substituent comprising from 1 carbon atom to about 10 carbon atoms selected from linear, branched, and cyclic alkyl moieties and substituted linear, branched, and cyclic alkyl moieties, to provide the compound of Formula (2Dc)

Formula 2Dc

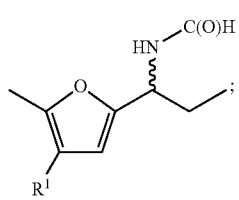

(b) hydrolyzing the compound (2Dc) by the treatment with aqueous base, yielding the free base racemic compound (2Db), Formula 2Db

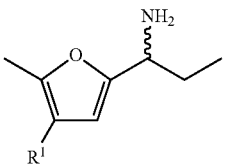

wherein R¹ is defined above; and (c) resolving the free base (2Db) prepared in step "b" by treatment with an acid of the formula H⁺[R-Anion⁻] in the presence of an alcohol of the formula R³OH, and optionally in the presence of a coacid, wherein, R¹ is defined above, "R-Anion" is an optically active monovalent anionic moiety capable of preferentially forming a salt of the R-isomer of the compound of Formula 2Db, and R³ is a linear, branched, or cyclic alkyl substituent of from 1 to 6 carbon atoms, yielding the salt compound of the Formula 2Da.

17. The Process of claim 16 wherein the compound of Formula 2Dd used in step "a" is 4-isopropyl-5-methyl-2-propionylfuran or 5-methyl-2-propionylfuran.

18. The process of claim 16 wherein, R¹ is hydrogen or isopropyl, and [R-Anion⁻] is the monovalent anion of D-tartarate.

19. The process of claim 16 comprising the additional step, before resolution step "c", of treating the free base racemate prepared in step "b" with an acid which preferentially precipitates a salt of the S-isomer of the compound of Formula 2D, followed by a filtration step, thereby increasing in the filtrate the ratio of R-isomer to S-isomer present in the compound of Formula 2Db.

20. The process of claim 19 wherein, in step "c" the acid of the Formula H⁺[R-Anion⁻] is D-tartaric acid.

21. The process of claim 16 wherein step "c" comprises a coacid which is HCl, malonic acid, acetic acid, formic acid, chloroacetic acid, or trifluoroacetic acid.

22. A process for preparing the compound of Formula 2B1

Formula 2B1

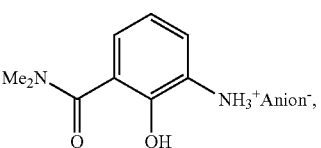

wherein "Anion⁻" is a monovalent anionic moiety, the process comprising;

(a) reacting 3-amino-2-hydroxy-N,N-dimethyl-benzamide (the compound of Formula IV(i)

IV(i)

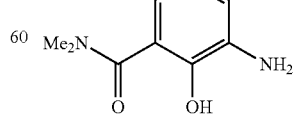

with an acid of the Formula H⁺Anion⁻, wherein "Anion⁻" is a monovalent anionic moiety, to form the compound of Formula 2B1

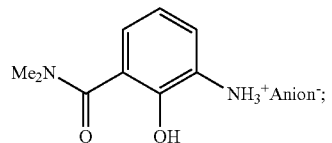

Formula 2B1

(b) optionally, precipitating the compound of Formula 2B1 and collecting the precipitate.

23. The process of claim 22 wherein step "a", formation of the salt compound of Formula 2B1 is carried out in a mixed solvent comprising methyl tertiary butyl ether (MTBE) and ethanol, and the acid is $H_2SO_4$, $H_3PO_4$, HBr, HCl, maleic acid, fumaric acid, malic acid, a sulfonic acid, oxalic acid, or tartaric acid.

24. The process of claim 22 wherein the acid is HCl (thus "Anion⁻" is Cl⁻), p-toluenesulfonic acid (thus "Anion⁻" is p-toluenesulfonic), oxalic acid (thus "Anion⁻" is oxalate), or tartaric acid (thus "Anion⁻" is (HO—C(O)—(HOCH)$_2$C(O)—O⁻).

\* \* \* \* \*